United States Patent [19]
Hodges et al.

[11] Patent Number: 5,744,336
[45] Date of Patent: Apr. 28, 1998

[54] DNA CONSTRUCTS FOR CONTROLLED TRANSFORMATION OF EUKARYOTIC CELLS

[75] Inventors: Thomas K. Hodges; Leszek A. Lyznik, both of West Lafayette, Ind.

[73] Assignee: Purdue Research Foundation, West Lafayette, Ind.

[21] Appl. No.: 612,551

[22] Filed: Mar. 8, 1996

Related U.S. Application Data

[62] Division of Ser. No. 10,997, Jan. 29, 1993, Pat. No. 5,527,695.

[51] Int. Cl.$^6$ .............................. C07H 21/04; C12N 15/63
[52] U.S. Cl. .................... 435/172.3; 536/23.1; 536/24.1; 536/24.2
[58] Field of Search ................................ 435/91.1, 172.3, 435/243, 320.1, 419, 91.4; 536/23.1, 24.1, 24.2, 23.5

[56] References Cited

FOREIGN PATENT DOCUMENTS

WO 91/09957  7/1991  WIPO .

OTHER PUBLICATIONS

"Directed Excision of a Transgene From The Plant Genome", Russell, et al., *Mol. Gen. Genet.,* (1992), 234:49–59.

"Homologous Recombination Between Plasmid DNA Molecules in Maize Protoplasts", Lyznik, et al., *Mol. Gen. Genet.,* (1991), 230:209–218.

"The FLP Recombinase of Yeast Catalyzes Site–Specific Recombination in the Drosophila Genome", Golic and Lindguist, *Cell* vol. 59, Nov. 3, 1989, 499–509.

"Exchange of Gene Activity in Transgenic Plants Catalyzed by the Cre–lox Site–Specific Recombination System", Bayley, et al., *Plant Molecular Biology,* 18:353–361, 1992.

"Maize Polyubiquitin Genes: Structure, Thermal Perturbation of Expression and Transcript Splicing, and Promoter Activity Following Transfer to Protoplasts by Electroporation", Christensen, et al., *Plant Molecular Biology,* 18:675–689, 1992.

"A Steroid–Inducible Gene Expression System for Plant Cells", Schena, et al., *Proc. Natl. Acad. Sci. USA,* vol. 88, pp. 10421–10425, Dec. 1991.

"Recombinase–Mediated Gene Activation and Site–Specific Integration in Mammalian Cells", O'Gorman, et al., *Reports,* 15 Mar. 1991, 1351–1355.

"Development of a Heat Shock Inducible Expression Cassette for Plants: Characterization of Parameters for Its Use in Transient Assays", Ainey and Key, *Plant Molecular Biology,* 1990, 14: 949–967.

"Host Gene Transfer With Subsequent Removal of the Selection Gene From The Gene", Dale and Ow, *Proc. Natl. Acad. Sci. USA,* vol. 88, Dec. 1991, pp. 10558–10562.

"Selection–Gene–Free Transgenic Plants", NTIS Patent Application Serial No. 07/725,320, Filed Jul. 8, 1991, by U.S. Department of Agriculture, Washington, D.C. (PB92–10550).

"Site–directed recombination in the genome of transgenic tobacco", Odell et al., *Mol. Gen. Gent.,* 223:369–378, Sep., 1990.

"The role of the loxP spacer region in P1 site–specific recombination", Hoess et al., *Nucleic Acid Research,* vol. 14, No. 5, pp. 2287–2300, 1986.

(List continued on next page.)

*Primary Examiner*—David Guzo
*Assistant Examiner*—William Sandals
*Attorney, Agent, or Firm*—Barnes & Thornburg

[57] ABSTRACT

DNA constructs are provided for the creation of transgenic eukaryotic cells. These DNA constructs allow a more precise and effective transformation procedure by enabling the targeting of DNA sequences for insertion into a particular DNA locus, while enabling the removal of any randomly inserted DNA sequences that occur as a by product of known transformation procedures.

15 Claims, 11 Drawing Sheets

OTHER PUBLICATIONS

"Transformation of Maize Cells and Regeneration of Fertile Transgenic Plants", Gordon–Kamm, *The Plant Cell*, vol. 2, pp. 603–618, Jul., 1990.

"Altering the Genome by Homologous Recombination", Capecchi, *Science*, vol. 244, pp. 1288–1292, 1989.

"Gene Targeting in Plants", Paszkowski et al., *The EMBO Journal*, vol. 7, No. 13, pp. 4021–4026, 1988.

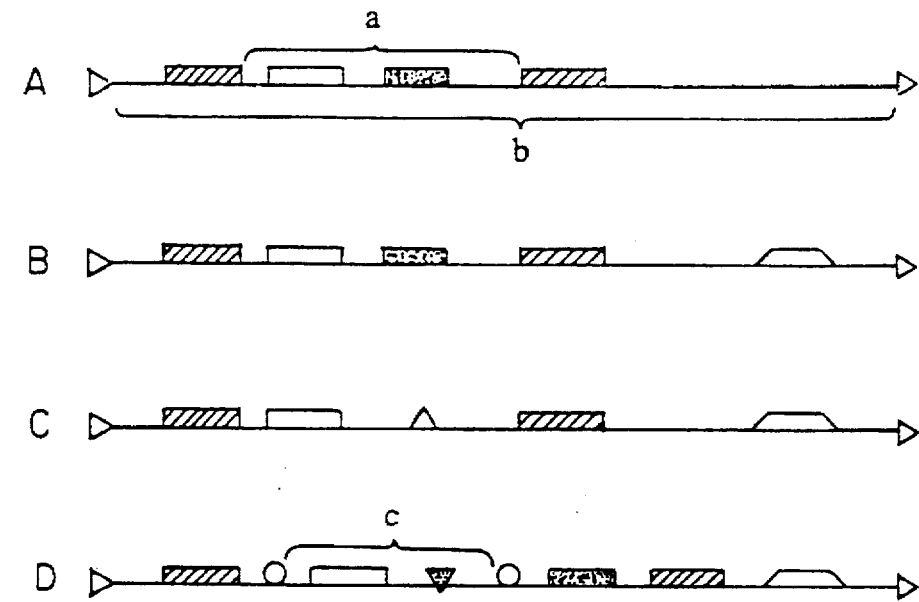
| ▷ | 1st RECOMBINATION TARGET SEQUENCE |
| ▨ | HOMOLOGOUS REGION |
| ▭ | 1st SELECTABLE MARKER GENE |
| ▦ | DNA SEQUENCE OF INTEREST |
| ○ | 2nd RECOMBINATION TARGET SEQUENCE |
| △ | POLYLINKER REGION |
| ▽ | 2nd RECOMBINASE GENE |
| ⬭ | 1st RECOMBINASE GENE |
| a - | DNA TARGETED FOR INSERTION VIA HOMOLOGOUS RECOMBINATION |
| b - | MULTIFUNCTIONAL DNA SEQUENCE |
| c - | EXCISABLE SELECTION REGION |
FIG. IA

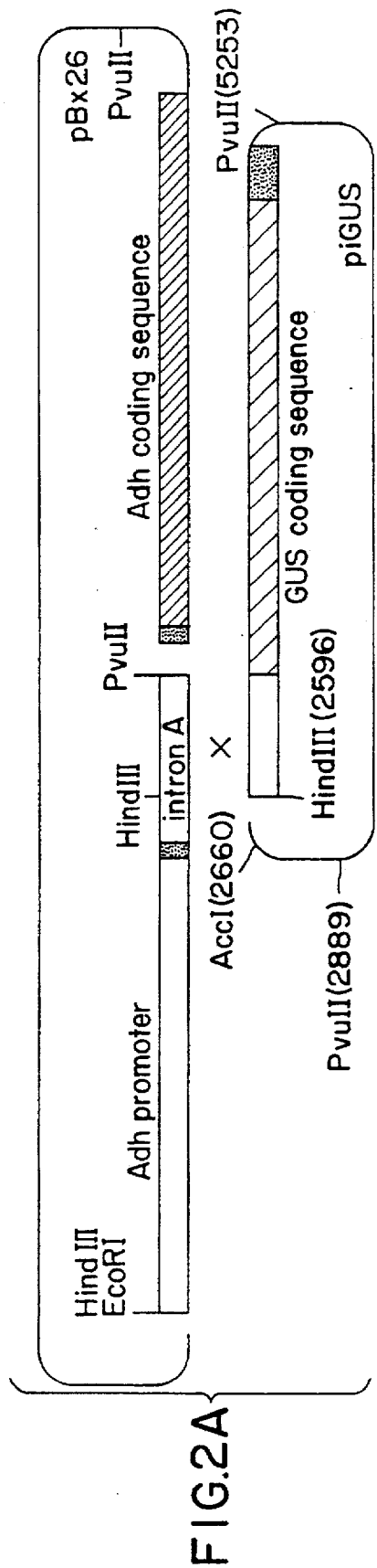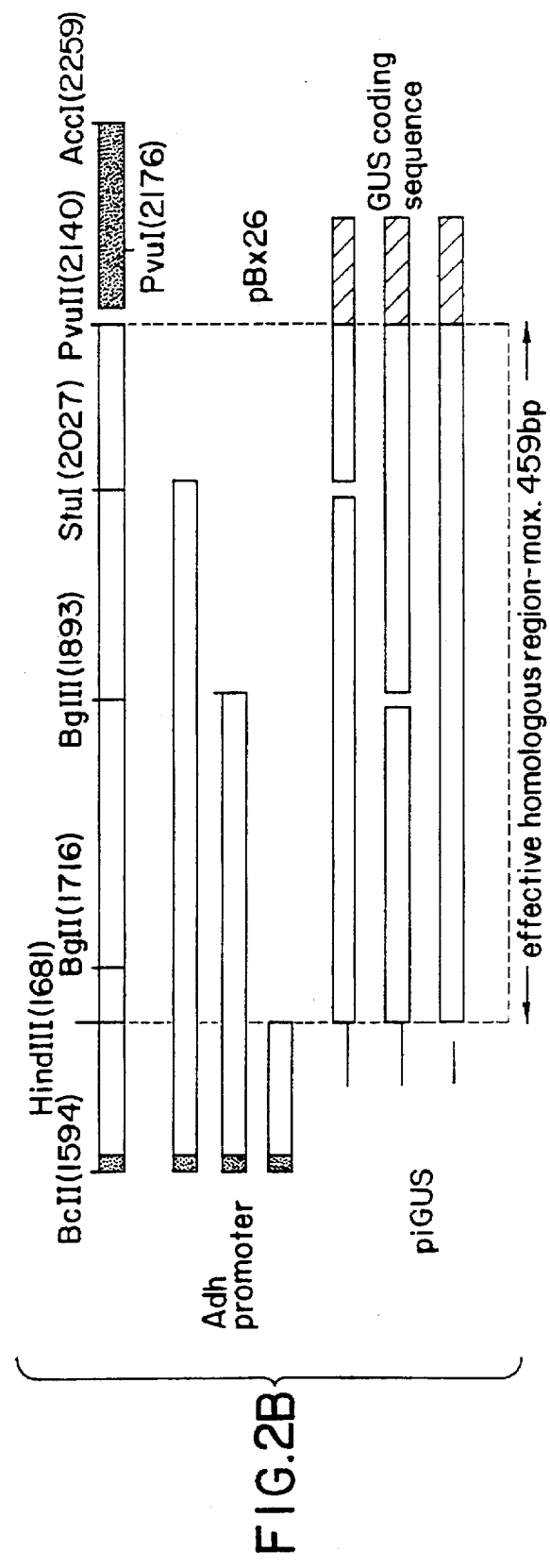
FIG. 2A
FIG. 2B

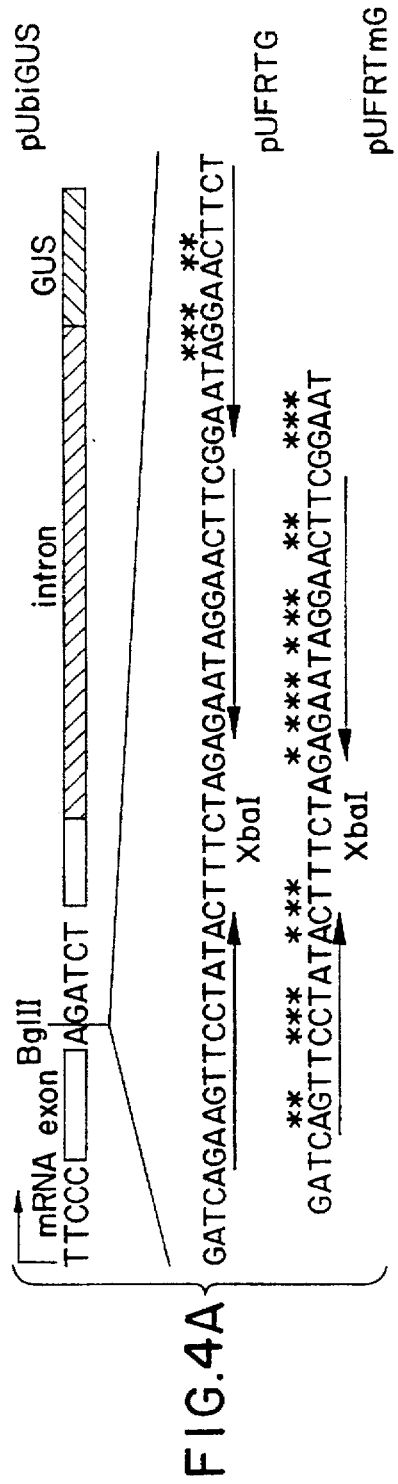
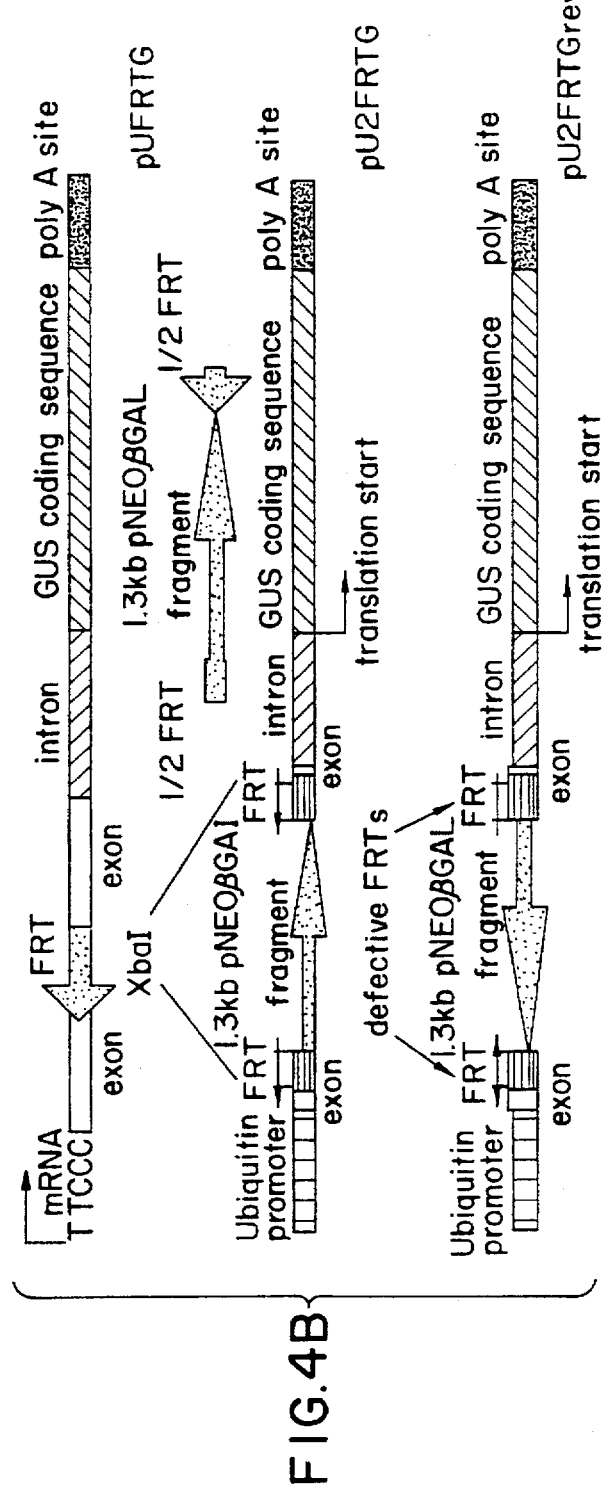
FIG.4A
FIG.4B

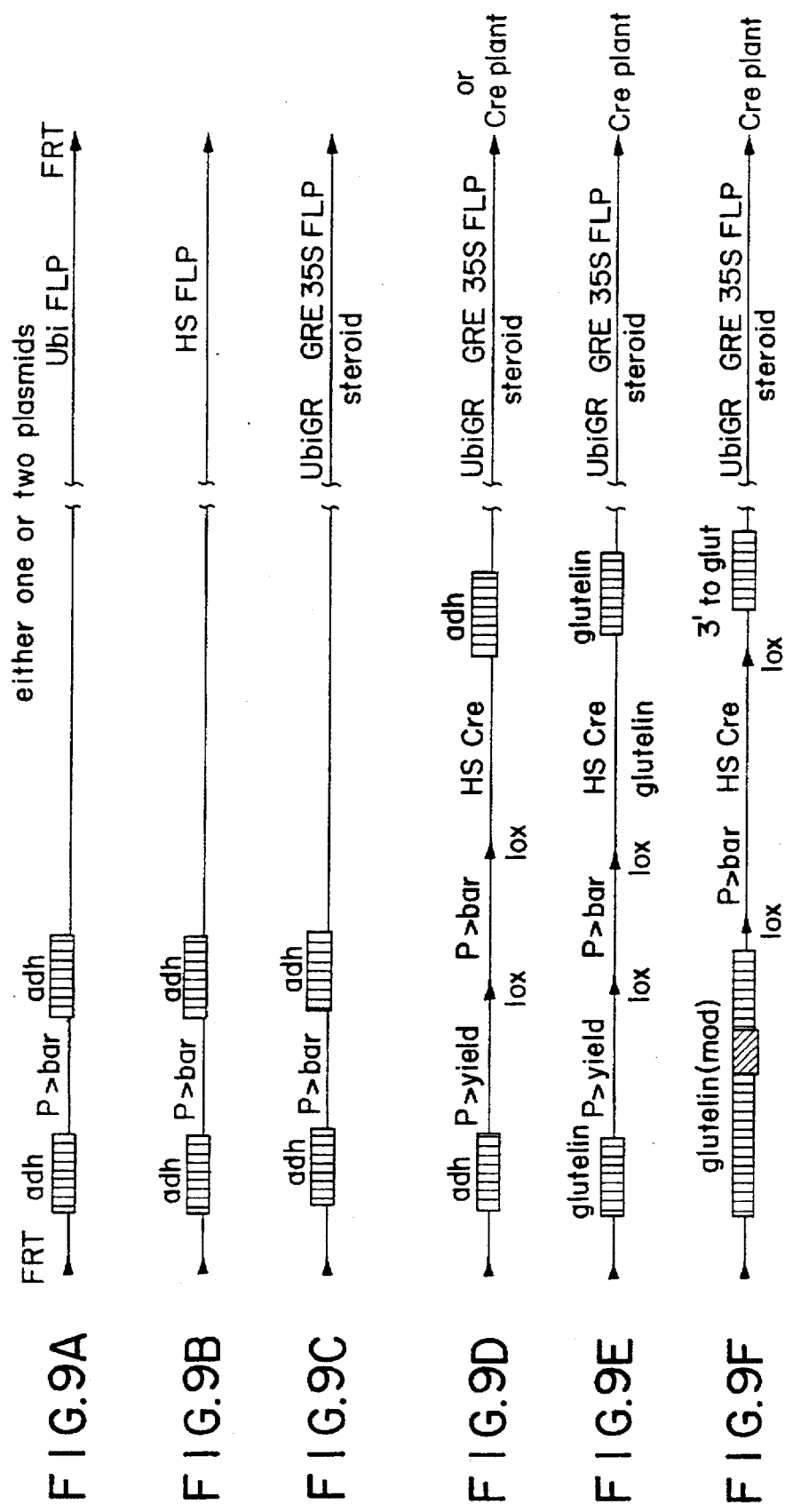

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

GGGGTTTCTA CAGGACG                            17

( 2 ) INFORMATION FOR SEQ ID NO:2:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:2:

CCTCACAGGC TCATCTCG                           18

( 2 ) INFORMATION FOR SEQ ID NO:3:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:3:

GTGATCAGAA GTTCCTATTC CGAAGTTCCT ATTCTCTAGA AA           42

( 2 ) INFORMATION FOR SEQ ID NO:4:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

CTGATCAGAA GTTCCTATAC TTTCTAGA                    28

( 2 ) INFORMATION FOR SEQ ID NO:5:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

CCCCAACCTC GTG                                                                                         13

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CCCGTGCAGC TGCGGTGGCA                                                                                  20

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CAACTGCAGC CCAAGCTTCC ACCATG                                                                           26

( 2 ) INFORMATION FOR SEQ ID NO:8:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CTTCTGCAGG TCGACTCTAG GATCCCCGGG TTCGAAATCG ATAAGCTTCC ACCATG                                           56

( 2 ) INFORMATION FOR SEQ ID NO:9:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GATCAGAAGT TCCTATACTT TCTAGAGAAT AGGAACTTCG GAATAGGAAC TTCT                                             54

( 2 ) INFORMATION FOR SEQ ID NO:10:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GATCAGTTCC TATACTTTCT AGAGAATAGG AACTTCGGAA T                                                           41

DNA CONSTRUCTS FOR CONTROLLED TRANSFORMATION OF EUKARYOTIC CELLS

This is a division of application Ser. No. 08/010,997, filed Jan. 29, 1993 now U.S. Pat. No. 5,527,695.

BACKGROUND AND SUMMARY OF THE INVENTION

This invention relates to a method of transforming eukaryotic cells. More particularly, this invention relates to the use of DNA constructs designed to insert a particular DNA fragment into a chosen locus of the host cell's DNA.

Through the use of recombinant DNA technology, foreign DNA sequences can be inserted into an organism's genome to alter the phenotype of the organism. A variety of different procedures have been described and utilized to produce stably transformed eukaryotic cells. All of these procedures are based on first introducing the foreign DNA into the eukaryotic cell, followed by isolation of those cells containing the foreign DNA integrated into the eukaryotic cell's DNA.

Unfortunately, all current higher eukaryotic cell transformation procedures produce transformed cells that contain the introduced foreign DNA inserted randomly and throughout the genome and in multiple copies. This random insertion of introduced DNA into the genome of host cells can be lethal if the foreign DNA happens to insert into, and thus mutate, a critically important native gene. In addition, even if the random insertion event does not impair the functioning of a host cell gene, the expression of an inserted foreign gene may be influenced by "position effects" caused by the surrounding genomic DNA. Thus a gene could be inserted into a site where the position effects are strong enough to prevent the synthesis of an effective amount of product from the introduced gene. Finally, because over-production of a gene product can have deleterious effects on the cell, genetic engineers typically wish to control the copy number of the inserted DNA, often only desiring the insertion of a single copy of the DNA sequence.

For these reasons a transformation system is desired that allows a gene to be targeted to a specific site of the host's genome. Preferably, such a system would also provide a means of preventing or subsequently removing any randomly inserted DNA sequences.

The present invention enables the targeting of a length of DNA to a specific non-lethal site in the host cell's genome, and provides for the removal of any randomly inserted DNA sequences. In addition, a proper selection of the targeted site can minimize position effects, enabling an inserted gene to synthesize an effective amount of its protein product. Therefore, this invention allows a much more precise and effective system of genetic engineering than is currently possible.

Additional objects, features, and advantages of the invention will become apparent to those skilled in the art upon consideration of the following detailed description of preferred embodiments exemplifying the best mode of the invention as presently perceived.

BRIEF DESCRIPTION OF THE DRAWINGS

FIGS. 1A and 1B are schematic representations of DNA constructs in accordance with this invention.

FIGS. 2A and 2B illustrate plasmid constructions and general strategies for recombination experiments.

FIGS. 4A and 4B illustrate the structure of the FRT site-containing vectors including the sequence of the complete FRT site (SEQ ID NO: 9) and the sequence of the minimal FRT site (SEQ ID NO: 10).

FIG. 9 illustrates examples of DNA constructs in accordance with this invention.

DETAILED DESCRIPTION OF THE INVENTION

Figure 1B:
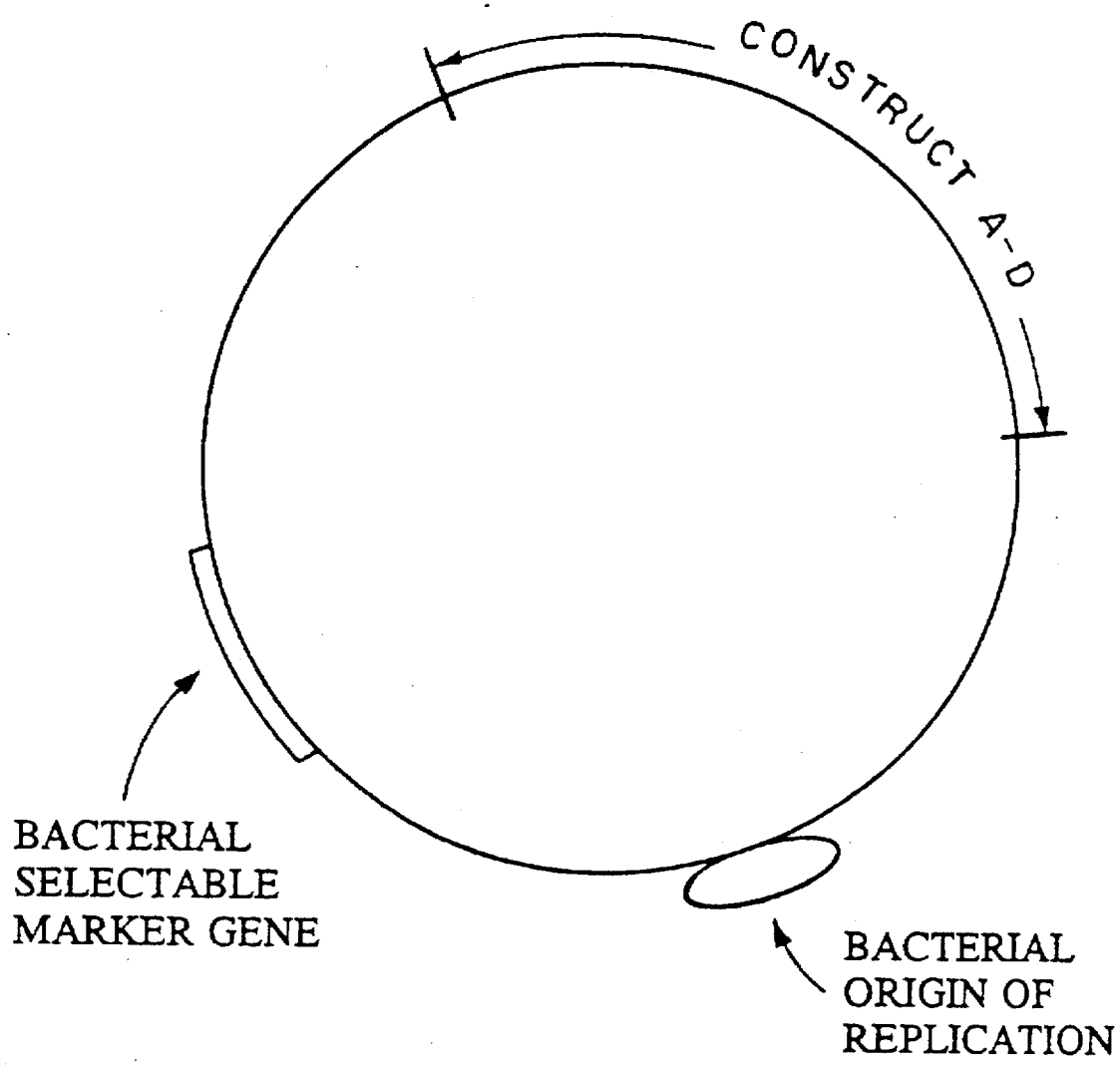

In accordance with one preferred embodiment of the present invention, eukaryotic cells are transformed with DNA sequences that are targeted to a predetermined sequence of the eukaryote's DNA. Typically the introduced DNA sequences will constitute entire functional genes.

Eukaryotic cells can also be transformed with other DNA sequences such as gene transcription and translation regulatory sequences. Transcription and translation regulatory sequences are those DNA sequences necessary for efficient expression of a gene product. In general such regulatory elements can be operably linked to any gene to control the gene's expression, the entire unit being referred to as the "expression cassette." An expression cassette will typically contain, in addition to the coding sequence, a promoter region, a translation initiation site and a translation termination sequence. Unique endonuclease restriction sites may also be included at the ends of an expression cassette to allow the cassette to be easily inserted or removed when creating DNA constructs.

The expression of a gene is primarily directed by its own promoter, although other DNA regulatory elements are necessary for efficient expression of a gene product. Promoter sequence elements include the TATA box consensus sequence (TATAAT), which is usually 20 to 30 base pairs (bp) upstream of the transcription start site. In most instances the TATA box is required for accurate transcription initiation. By convention, the transcription start site is designated +1. Sequences extending in the 5' (upstream) direction are given negative numbers and sequences extending in the 3' (downstream) direction are given positive numbers.

Promoters can be either constitutive or inducible. A constitutive promoter controls transcription of a gene at a constant rate during the life of a cell, whereas an inducible promoter's activity fluctuates as determined by the presence (or absence) of a specific inducer. The regulatory elements of an inducible promoter are usually located further upstream of the transcriptional start site than the TATA box. Ideally, for experimental purposes, an inducible promoter should possess each of the following properties: a low to nonexistent basal level of expression in the absence of inducer, a high level of expression in the presence of inducer, and an induction scheme that does not otherwise alter the physiology of the cell. The basal transcriptional activity of all promoters can be increased by the presence of "enhancer" sequences. Although the mechanism is unclear, certain defined enhancer regulatory sequences are known, to those familiar with the art, to increase a promoter's transcription rate when the sequence is brought in proximity to the promoter.

The creation of a transformed cell requires that the DNA be physically placed within the host cell. Current transformation procedures utilize a variety of techniques to introduce DNA into a cell. In one form of transformation, the DNA is microinjected directly into cells though the use of micropipettes. Alternatively, high velocity ballistics can be used to propel small DNA associated particles into the cell. In another form, the cell is permeablized by the presence of polyethylene glycol, thus allowing DNA to enter the cell through diffusion. DNA can also be introduced into a cell by fusing protoplasts with other entities which contain DNA. These entities include minicells, cells, lysosomes or other fusible lipid-surfaced bodies. Electroporation is also an accepted method for introducing DNA into a cell. In this technique, cells are subject to electrical impulses of high field strength which reversibly permeabilizes biomembranes, allowing the entry of exogenous DNA sequences.

In addition to these "direct" transformation techniques, transformation can be performed via bacterial infection using *Agrobacterium tumefaciens* or *Agrobacterium rhizogenes*. These bacterial strains contain a plasmid (called Ti or Ri respectively) which is transmitted into plant cells after infection by Agrobacterium. One portion of the plasmid, named transferred DNA (T-DNA), is then integrated into the genomic DNA of the plant cell. This system has been extensively described in the literature and can be modified to introduce foreign genes and other DNA sequences into plant cells.

Agrobacterium-mediated transformation works best with dicotyledonous diploid plant cells whereas the direct transformation techniques work with virtually any cell. Direct transformation techniques can be used to transform haploid cells obtained from immature inflorescences of plants.

Transformed cells (those containing the DNA inserted into the host cell's DNA) can be selected from untransformed cells if a selectable marker was included as part of the introduced DNA sequences. Selectable markers include genes that provide antibiotic resistance or herbicide resistance. Cells containing these genes are capable of surviving in the presence of antibiotic or herbicide concentrations that kill untransformed cells. Examples of selectable markers include the bar gene which provides resistance to the herbicide Basta, the nptII gene which confers kanamycin resistance and the hpt gene which confers hygromycin resistance.

Once a transformed plant cell is generated, an entire plant can be obtained through cell culturing techniques. Individual cultured cells divide to give rise to an undifferentiated mass of cells called callus tissue. Once callus tissue is formed, shoots and roots may be induced from the callus by techniques known to those familiar with the art, and the resulting plantlets can be planted. Alternatively, somatic embryo formation can be induced in the callus tissue. These somatic embryos germinate as natural embryos to form plants. All the transformation techniques described above have the limitation that they result in multiple copies inserted, and (but to a lesser extent in Agrobacterium-mediated transformations) result in foreign DNA insertions throughout the genome.

The present invention enables the targeting of a length of DNA to a specific site in the host cell's genome that is non-lethal, and provides for the removal of any introduced DNA sequences randomly inserted into the genome. Presumably the selected target site will also allow the inserted gene to produce its protein product in an amount sufficient to produce the desired effect.

The first element of the invention involves targeting the gene to a specific site in the host cell's genome. Targeting will be carried out via "homologous recombination." Homologous recombination is a reaction between any pair of DNA sequences having a similar sequence of nucleotides (homologous sequences), where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases.

Introduced DNA sequences can be targeted via homologous recombination by linking the DNA of interest to sequences sharing homology with endogenous sequences of the host cell. Once the DNA enters the cell, the two homologous sequences can interact to insert the introduced DNA at the site where the homologous genomic DNA sequences were located. Therefore, the choice of homologous sequences contained on the introduced DNA, will determine the site where the introduced DNA is integrated via homologous recombination. For example, if the DNA sequence of interest is linked to DNA sequences sharing homology to a single copy gene of the host eukaryotic cell, the DNA sequence of interest will be inserted via homologous recombination at only that single specific site. However, if the DNA sequence of interest is linked to DNA sequences sharing homology to a multi-copy gene of the host eukaryotic cell, then the DNA sequence of interest can be inserted via homologous recombination at each of the specific sites where a copy of the gene is located. Preferably, the predetermined host DNA site of insertion is a non-essential endogenous gene present in high copy number, e.g. a storage protein gene.

DNA can be inserted into the genome by a homologous recombination reaction involving either a single reciprocal recombination (resulting in the insertion of the entire length of the introduced DNA) or through a double reciprocal recombination (resulting in the insertion of only the DNA located between the two recombination events). For example if one wishes to insert a foreign gene into the genomic site where the gene encoding alcohol dehydrogenase (the adh gene) is located, the introduced DNA should contain sequences homologous to the genomic adh gene. A single homologous recombination event would then result in the entire introduced DNA sequence being inserted into the genomic adh gene. Alternatively, a double recombination event can be achieved by flanking each end of the DNA sequence of interest (the sequence intended to be inserted into the genome) with DNA sequences homologous to the adh gene. A homologous recombination event involving each of the homologous flanking regions will result in the insertion of the foreign DNA. Thus only those DNA sequences located between the two regions sharing genomic homology become integrated into the genome.

Although introduced sequences can be targeted for insertion into a specific genomic site via homologous recombination, in higher eukaryotes homologous recombination is a relatively rare event compared to random insertion events. In plant cells, foreign DNA molecules find homologous sequences in the cell's genome and recombine at a frequency of 0.5–4.2×10$^{-4}$ (the number of targeted events divided by the number of random integrations events). Thus any transformed cell that contains an introduced DNA sequence integrated via homologous recombination will also likely contain numerous copies of randomly integrated introduced DNA sequences. Therefore to maintain control over the copy number and the location of the inserted DNA, these randomly inserted DNA sequences must be removed.

One manner of removing these random insertions is to utilize a site-specific recombinase system. In general, a site specific recombinase system consists of three elements: two pairs of DNA sequence (the site-specific recombination sequences) and a specific enzyme (the site-specific recombinase). The site-specific recombinase will catalyze a recombination reaction only between two site-specific recombination sequences.

Depending on the orientation of the site-specific recombination sequences, intervening sequences will either be excised or inverted in the presence of the site specific recombinase. When the site-specific recombination sequences are orientated in opposite directions relative to one another (ie, inverted repeats) then any intervening sequences will be inverted relative to the other sequences in the genome. However, if the site-specific recombination sequences are orientated in the same direction relative to one another (ie, direct repeats) any intervening sequences will be deleted upon interaction with the site specific recombinase. Therefore, if direct repeats of the site-specific recombination sequences are present at both ends of DNA introduced into the cell, any random integration of these sequences can be subsequently removed by interaction of the site-specific recombination sequences with their site specific recombinase. Unlike the random integration event, a homologous recombination event will only integrate a portion of the introduced DNA. If this portion of the DNA does not contain both site-specific recombination sequences, then even in the presence of the site specific recombinase these sequences will remain integrated while the randomly integrated DNA sequences will be excised.

A number of different site specific recombinase systems can be used, including but not limited to the Cre/lox system of bacteriophage P1, the FLP/FRT system of yeast, the Gin recombinase of phage Mu, the Pin recombinase of *E. coli*, and the R/RS system of the pSR1 plasmid. The two preferred site specific recombinase systems are the bacteriophage P1 Cre/lox and the yeast FLP/FRT systems. In these systems a recombinase (Cre or FLP) will interact specifically with its respective site-specific recombination sequence (lox or FRT respectively) to invert or excise the intervening sequences. The sequence for each of these two systems is relatively short (34 bp for lox and 47 bp for FRT). Currently the FLP/FRT system of yeast is the preferred site specific recombinase system since it normally functions in a eukaryotic organism (yeast), and is well characterized. Applicants have reason to believe that the eukaryotic origin of the FLP/FRT system allows the FLP/FRT system to function more efficiently in eukaryotic cells than the prokaryotic site specific recombinase systems.

The FLP/FRT recombinase system has been demonstrated to function efficiently in plant cells. Experiments on the performance of the FLP/FRT system in both maize and rice protoplasts indicates that FRT site structure, and amount of the FLP protein present, affects excision activity. In general, short incomplete FRT sites leads to higher accumulation of excision products than the complete full-length FRT sites.

Site specific recombination systems can catalyze both intra- and intermolecular reactions in maize protoplasts, indicating that the system can be used for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

Another approach to manipulate the system is based on the entropic advantage of a unimolecular (excision) over a bimolecular (integration) reaction. By limiting the expression of the recombinase enzyme, the efficiency of the integrative recombination, the thermodynamically least favored event, can be reduced. Experiments in maize protoplasts indicate higher concentration of the FLP protein increased the efficiency of the excision reaction.

In one embodiment, a strong monocol promoter (the promoter of maize polyubiquitin gene) will be used to drive the expression of the FLP gene, and the introduced DNA construct will contain the short version of the FRT sites.

Although the site-specific recombination sequences must be linked to the ends of the introduced DNA, the gene encoding the site specific recombinase may be located elsewhere. For example, the recombinase gene could already be present in the plant's DNA or could be supplied by a later introduced DNA fragment either introduced directly into cells, or through cross-pollination.

One method for targeting the insertion of a DNA sequence into the DNA of a eukaryotic cell involves the use of a specific DNA transformation construct. Various DNA sequences can be included as components of these DNA transformation constructs, and are defined as follows. The "targeted DNA sequence" encompasses those nucleotide sequences present in the DNA construct, that are flanked by nucleotide sequences sharing homology to nucleotide sequences present in the eukaryotic cell (see FIG. 1A (bracket a)). The "DNA sequence of interest" is a subset of the targeted DNA sequence, consisting of DNA sequences intended to be permanently inserted into the DNA of a eukaryotic cell. The "excisable selection region" is also a subset of the targeted DNA sequence, comprising DNA sequences encoding a selectable marker flanked by a site-specific recombination sequence. The excisable selection region enables selection of homologously transformed cells, and the entire region can be removed after selection of cells transformed via homologous recombination. In addition, the excisable selection region may also contain a gene encoding a site-specific recombinase capable of interacting with the site-specific recombination sequence flanking the excisable selection region.

The selectable marker gene is operably linked to regulatory sequences capable of expressing the gene in the eukaryotic cell. The DNA sequence of interest is flanked by nucleotide sequences sharing homology with nucleotide sequences present in the eukaryotic cell. These flanking homologous sequences will induce a recombination event which inserts the targeted DNA region into a specific site of the eukaryotic cell's DNA.

The targeted DNA region of the transformation construct may comprise sequences encoding a selectable marker or a polylinker region. A polylinker is a short length of DNA that contains numerous different endonuclease restrictions sites located in close proximity. The presence of the polylinker is advantageous because it allows various expression cassettes to be easily inserted and removed, thus simplifying the process of making a construct containing a particular DNA fragment.

The above described transformation construct can also be part of a larger construct. The additional sequences of the larger construct comprising DNA sequences capable of replicating the entire DNA molecule in a bacterial host and DNA sequences encoding a bacterial selectable marker (such as genes encoding for ampicillin or tetracycline resistance). This larger construct, ideally a plasmid, can be used to transform bacterial cells. These transformed bacterial cells can then be cultured to produce large quantities of the plasmid DNA. The specific transformation construct can then be isolated using techniques well known to those familiar with the art.

Targeting the insertion of a DNA sequence into a specific site of a host cell's DNA requires introduction of the transformation construct into the cell by one of the known transformation techniques. Once the DNA has entered the host cells, the cells can be cultured under a selection scheme that kills any cells not containing the selectable marker. After selection for transformed cells, introduction of site specific recombinase activity will excise the randomly inserted DNA constructs. These excised DNA fragments will subsequently be lost from the cell via the action of nucleases. Those cells that have integrated the introduced DNA via homologous recombination will retain the integrated DNA even in the presence of recombinase activity. These cells can subsequently be isolated and cultured to proliferate callus and regenerate new tissues, organs and organisms (plants or animals).

A recombinase gene cassette is used to generate the recombinase activity needed to excise the randomly integrated DNA fragments. This recombinase gene cassette can either be physically linked to the introduced DNA sequences, already present in the host cell's genome, or subsequently introduced as a separate DNA molecule. However, the timing of recombinase expression relative to the integration process may be a critical factor in producing the desired end product. Homologous recombination takes place in both animal and plant cells, within approximately 30 minutes after transformation. An additional 3–4 hours is required for the production of detectable amounts of foreign gene product. Applicants initially assume that upon co-introduction of the FLP gene and the transformation construct into protoplasts, integration and homologous recombination will be completed prior to significant FLP recombinase activity. If the co-introduction strategy is too inefficient, strategies can be utilized that control the recombinase gene expression.

In one embodiment of the invention, recombinase activity is delayed for a sufficient time interval to allow the gene of interest to be integrated into its specific site via homologous recombination.

One way of delaying the activity of the recombinase comprises operably linking the recombinase gene to an inducible promoter. Inducible promoters include any promoter capable of increasing the amount of gene product produced, by a given gene, in response to exposure to an inducer. Inducible promoters are known to those familiar with the art and a variety exist that could conceivably be used to drive expression of the recombinase gene.

Two preferred inducible promoters are the heat shock promoter and the glucocorticoid system. Promoters regulated by heat shock, such as the promoter normally associated with the gene encoding the 70-kDa heat shock protein, can increase expression several-fold after exposure to elevated temperatures. The heat shock promoter could be used as an environmentally inducible promoter for controlling transcription of the FLP gene. The glucocorticoid system also functions well in triggering the expression of genes including recombinase genes. The system consists of a gene encoding glucocorticoid receptor protein (GR) which in the presence of a steroid hormone forms a complex with the hormone. This complex then binds to a short nucleotide sequence (26 bp) named the glucocorticoid response element (GRE), and this binding activates the expression of linked genes.

The glucocorticoid system can be included in the DNA transformation construct as a means to induce recombinase expression. In one embodiment utilizing the glucocorticoid system, the entire introduced DNA is flanked by direct repeats of either the lox or FRT site-specific recombination sequence. Located between these direct repeats are several elements including: the DNA sequence of interest flanked by sequences sharing homology to host cell nucleotide sequences, the recombinase gene sequence (Cre or FLP) driven by a truncated (and therefore ineffective) promoter containing at least one GRE sequence positioned upstream from the truncated promoter, a selectable marker gene driven by a constitutive promoter and the glucocorticoid receptor (GR) gene driven by a constitutive promoter. Following transfer of this linear piece of DNA into the cell's nucleus, the gene of interest will be inserted into its specific site via homologous recombination. Multiple random insertions of the entire piece of DNA will also occur throughout the genome. The resulting cells will then be cultured in the presence of a selection agent to isolate transformed cells. Once these cells/calli have been selected, they will then be treated with the steroid hormone, glucocorticoid or one of its synthetic equivalents such as dexamethasone. The steroid hormone will associate with the constitutively produced GR protein to bind to the GRE elements, thus stimulating expression of the recombinase gene (eg. Cre or FLP). Production of the recombinase will then trigger the excision of randomly inserted DNA sequences, but will not effect any insertion resulting from the homologous recombination event.

Inducible promoters are not the only means of triggering the production of recombinase activity. Other potential means of delaying the functional activity of a gene product are known to those familiar with the art.

Once recombinase activity has been triggered and the randomly inserted DNA has been removed, various means can be used to isolate those cells/calli that contain the DNA of interest. Using standard techniques known to those familiar with the field, eg. Southern blotting and polymerase chain reaction, DNA can be isolated from individual calli and screened for the presence of the DNA of interest. An alternative method of screening to identify desired transformants utilizes a visible phenotypic marker located on the homologously inserted DNA. Then only those calli or regenerated plants that express the phenotype have the desired DNA insertion.

In an alternative selection scheme the DNA sequences inserted via a homologous recombination event also include sequences encoding a selectable marker. This DNA transformation construct can be used to transfect cells, and transformed cells can be isolated by culturing the cells in the presence of selection agents. Once transformed cells have been isolated, and the randomly inserted DNA sequences have been removed, the cells can be exposed to a second round of selection. Only those cells transformed via a homologous recombination event will retain the selectable marker gene, and will survive the second round of selection and culturing.

In one embodiment, as shown in FIG. 1A(A), a recombinant DNA molecule for use in transforming eukaryotic cells comprises a multifunctional DNA sequence flanked by two directly repeated site-specific recombination sequences. The multifunctional DNA sequence comprises a targeted DNA region flanked on each end by nucleotide sequences sharing homology to nucleotide sequences present in the eukaryotic cell to be transformed. The targeted DNA region comprises a selectable marker gene under the control of a constitutive promoter and a DNA sequence of interest (the DNA sequences desired to be inserted into the cells' DNA).

Once the multifunctional DNA sequence is introduced into the cell, the entire molecule can be inserted into the host cell's DNA via a random recombination event, or alternatively the targeted DNA region can be inserted via a homologous recombination event. Selection for the expression of the selectable marker gene product will isolate both of these types of transformed cells. Subsequent site specific recombinase activity, capable of interacting with the site-specific recombination sequences flanking the multifunctional DNA sequence, can then be generated within the cell. This recombinase activity will cause the excision of all the randomly inserted recombinant DNA molecules. Once the randomly inserted DNA sequences have been removed, exposure of the cells to a second round of selection for the selectable marker will isolate those cells containing the targeted DNA region integrated via homologous recombination.

One manner of generating the site specific recombinase activity involves retransforming the cells with a second DNA construct that encodes a site specific recombinase. Alternatively, the recombinase gene can be included on the original introduced DNA construct as shown in FIG. 1A(B). If the site specific recombinase gene is co-introduced with the original DNA construct, the expression of the recombinase gene may be regulated by an inducible promoter. Potential inducible promoters include the heat shock promoter and the glucocorticoid system.

As shown in FIG. 1A(C), the transformation construct can also include a polylinker region located in the targeted DNA sequence. The addition of a polylinker region promotes the ease of constructing unique DNA molecules. Through the use of specific nucleotide restriction enzymes, gene cassettes and other DNA sequences can be inserted into the polylinker region. Any DNA sequence inserted into the polylinker can then be targeted for insertion into a host cell's DNA via homologous recombination.

In another embodiment, two different site specific recombination systems, eg., cre/lox and FLP/FRT are used in combination to select for cells transformed via homologous recombination. DNA sequences must first be introduced into the host cells, using techniques known to those familiar with the art. These cells will then be subjected to a first round of selection to isolate cells containing the introduced DNA integrated into the cell's DNA. This round of selection will yield a majority of cells that have the introduced DNA randomly inserted into the cell's genome as well as a small number of cells having the introduced DNA integrated into the cell's genome by homologous recombination. It is highly probable that those cells containing the introduced DNA integrated via a homologous recombination event will also have the introduced DNA randomly inserted at different locations of the genome. These randomly integrated sequences can be removed through the use of a site specific recombination system.

The second round of selection occurs after the randomly inserted DNA sequences have been removed from the host cell's genome. This second round of selection identifies those cells that have a portion of the original introduced DNA integrated into the predetermined site of the host cell's DNA by homologous recombination. A second separate site specific recombination system can then be utilized to remove the DNA sequences that were required for the second round of selection, leaving only desired DNA sequences still integrated into the host cell's DNA.

To carry out this process the desired DNA sequences targeted for integration into the host cell's genome must be operably linked to a number of functional DNA sequences. First of all, any introduced DNA sequences that are likely to be randomly inserted into the host genome must be flanked by two directly repeated site-specific recombination sequences. In this construction, any randomly integrated DNA sequence can be excised through the interaction of a site specific recombinase with its site-specific recombination sequence. A number of different site specific recombinase systems can be used, including the Cre/lox system of the bacteriophage P1, the FLP/FRT system of yeast, the Gin recombinase of phage Mu, and the R/RS system of pSR1 plasmid.

In one preferred embodiment the introduced DNA consists of a multifunctional DNA sequence flanked by direct repeats of a first site-specific recombination sequence (see FIG. 1A). The DNA located between the two site-specific recombination sequences comprises, a gene encoding a first site specific recombinase gene capable of recognizing the first recombinase target sequence, and a targeted DNA sequence. The targeted DNA sequence (FIG. 1A (bracket a)) is flanked by nucleotide sequences sharing homology to nucleotide sequences present in the eukaryotic cells to be transformed. These "homologous regions" function to initiate and terminate a homologous recombination reaction that will insert the DNA sequences located between the two homologous regions into the host cell's DNA. Preferably, the DNA sequence located between the two homologous regions comprises a DNA sequence of interest, and a "excisable selection region. The DNA sequence of interest consists of DNA sequences that are desired to be permanently inserted into the host cell's DNA. The "excisable selection region" (FIG. 1A (bracket c)) contains DNA sequences encoding products that are required for selection of the homologous recombination event and is flanked by direct repeats of a site-specific recombination sequence.

The excisable selection region is no longer needed once the cells-containing the homologous recombination event have been selected. Therefore, these sequences can be removed after the second round of selection through the use of a second site-specific recombinase system. Optimally, a different site-specific recombinase system is utilized than the one use to excise the randomly inserted DNA sequences. Thus in one form of the invention, the excisable selection region is flanked by direct repeats of a second site-specific recombination sequence, and comprises a gene encoding a selectable marker, and a gene encoding a second site specific recombinase gene capable of recognizing the second site-specific recombination sequence. An example of this embodiment is shown in FIG. 1A(D). The entire second site-specific recombinase system is located within the targeted region. The DNA sequences that are desired to be permanently inserted into the host cell's DNA are located outside the second recombinase system, but within the targeted region. In this transformation construct the expression of the second recombinase gene is preferably controlled by an inducible promoter.

Once the construct, shown in FIG. 1A(D), is introduced into a cell, transformed cells can be selected through the use of the selectable marker gene. After the first round of selection, the expression of the first recombinase activity will result in the removal of randomly inserted DNA sequences. Exposure of these cells to a second round of selection will isolate those cells which have the targeted region integrated into the cell's DNA via a homologous recombination event. These cells will contain the excisable selection region and the DNA sequences of interest. Inducing the production of the second recombinase will result in the excision of the excisable selection region leaving only the DNA sequence of interest. Thus a transformed cell can be created that contains only the desired genes integrated into a predetermined site of the host cell's DNA.

Although including the site-specific recombinase genes on the introduced DNA sequence is convenient, this is not necessary. These genes could be supplied on a separately introduced piece of DNA or could already be present in the host cell's DNA or could be introduced by cross pollination. Typically all the genes contained on the introduced DNA will be linked to regulatory sequences capable of expressing the gene's product in a eukaryotic cell. However, in preferred embodiments the expression of at least one of the site specific recombinase gene will be regulated by an inducible promoter.

For those transformation constructs that allow direct selection of cells transformed via a homologous recombination event, only those cells containing DNA integrated by homologous recombination should survive the second round of selection. However, the possibility does exist, because of some error in recombination, that the site specific recombinase activity will fail to remove all the randomly inserted DNA fragments. However, these anomalies will normally be detected by standard genomic DNA analysis and can thus be eliminated.

As shown in FIG. 1B, constructs A–D can be physically linked to additional sequences to form a circularized DNA molecule (a plasmid). These additional sequences would contain a gene cassette encoding a bacterial selectable marker and a bacterial origin of replication. This plasmid is useful in generating large amounts of the A–D DNA constructs. The procedure consists of using this plasmid to transform bacterial cells, growing the bacterial cells under selection for the presence of the plasmid and then finally isolating the plasmid from the replicated bacterial cells. In order to prevent integration of unnecessary plasmid DNA that is outside the site-specific recombination sequences, the plasmid will also contain restriction endonuclease sites that allow the removal of the plasmid sequences prior to transformation.

The following examples are intended to illustrate but not limit the invention. All plasmid constructs are harbored in E. coli strain HB101 cultures maintained in our laboratory under label corresponding to the plasmid construct designation.

EXAMPLE 1

Homologous Recombination between Plasmid DNAs

Materials and methods

Plasmid constructions. A 6.8 kb Bam HI-XhoI fragment of maize genomic DNA containing the adh1-S gene was inserted into the BamHI-SacI sites of pBR322 to yield pBx26. (See FIG. 2A.) A control vector pAeiGUS, was constructed by replacing the PvuII fragment of pBx26 (containing most adh1 coding sequences) with a SmaI-EcoRI fragment containing the ausA coding sequence and a nos polyA site. Thus, the construction contains a 1.5 kb BamHI-PvuII fragment from the Adh1 genomic clone with the first exon and intron A of the Adh1 gene fused in-frame to the gusA coding sequence; however, the gusA coding sequence still has its own start codon intact. The Adh1 promoter was removed by elimination of the HindIII fragment from pAeiGUS to create piGUS. piGUS still contained a 459 bp fragment of intron A in front of the gusA coding sequence, but the chimeric gusA gene was not active because of the absence of a promoter. The p35SGUS construction contained the GUS coding sequence driven by the CaMV 35S promoter. p35SiGUS was constructed by insertion of the blunt-ended SacII-PvuII fragment of pBx26 containing intron A into the SmaI site of p35GUS. pAGUS was constructed by insertion of the BamHI-Csp45 promoter fragment of pBx26 into the BamHI-EcoRI site of pB1201.

FIGS. 2A and B show plasmid constructions and general strategy of recombination experiments. pBx26 (11.5 kb) (FIG. 2A) was doubly digested with relevant restriction enzymes and EcoRI to standardize the 5' end of the DNA molecule participating in the recombination reaction. This fragment (total size 2.1 kb) contained the promoter (dotted bar), first exon (closed bar), and intron A (open bar) of the maize Adh1 genomic clone. piGUS contained the HindIII-PvuII fragment of intron A followed by the β-glucuronidase (GUS) coding sequence and the nopaline synthase (NOS) polyadenylation site. The PvuII site was destroyed after ligation to the GUS coding sequence. Only those restriction sites applicable to the studies reported here are shown. The Adh1 coding sequence is not drawn to scale. (FIG. 2B) The effective homologous region (HindIII-PvuII fragment of intron A) contained restriction sites for BglII, BglIII, and StuI in the pBx26 and piGUS molecules. Numbers in parentheses represents the nucleotide position of the restriction sites on the pBx26 map.

All plasmid DNAs were prepared using the alkaline lysis method and purified by centrifugation in CsCl-ethidium bromide gradients as described in Maniatis et al. (1982). After the first centrifugation, the contaminating RNA was removed by incubation of the plasmid preparations for 1 h at room temperature with DNAse-free pancreatic RNAse. Finally, plasmid DNA was phenol extracted and dissolved in TE(10 mM TRIS-HCl, 1 mM EDTA pH 8.0) buffer (at 1 mg/ml) according to standard procedures.

Cell culture, protoplast isolation, and transformation

An A188xBMS cell suspension line of maize (Zea mays L.) was initiated from a type II friable callus as described by Kamo et al., Planta 172: 245–251 (1987). Suspension cultures were maintained on a gyratory shaker at 120 rpm and 25° C. in the dark. The cells were subcultured every week by placing 5 ml packed cell volume into 35 ml of N6 medium (Chu et al. Sci Sinica 5:659–668 1975) supplemented with 6 mM proline, 1 g/l casein hydrolysate, and 3.5 mg/l 2,4-dichlorophenoxyacetic acid (2,4-D). For protoplast isolation, 2 ml packed cell volume (pcv) were subcultured for 3 to 10 days before isolation in 41 ml of MS medium (Murashige and Skoog Physiol Plant 15: 413–497 1962) supplemented with 3.5 mg/l 2,4-D.

Approximately 5 ml pcv suspension cells were digested for 3 h in 20 ml MS medium containing 0.2M mannitol, 0.5 mg/l thiamine, 2 mg/l 2,4-D, 80 mM $CaCl_2$, 2% cellulase, 0.25% pectinase 0.1% (Worthington Biochemcial Co.) pectolyase Y-23 (Seishin Pharmaceutical Co.) pH 6.0. The protoplasts were filtered through a 48 um screen and pelleted by centrifugation at 50×g for 15 min. The protoplast pellet was suspended in 8 ml of protoplast culture medium (PCM); (Chourey and Zurawski, 1981, *Theor Appl. Genet* 59:341–344), containing 9% Ficoll (Ficoll 400, Sigma Chemical Co.), dispensed into two tubes, and overlaid with 4 ml of transformation solution (0.2M mannitol and 80 mM $CaCl_2$). After centrifugation at 75×g for 10 min, a band of protoplasts was collected at the interphase, and the concentration of protoplasts was adjusted to $1\times10^7$ protoplasts/ml with PCM. Transformation was carried out in 12 ml sterilized Falcon polystyrene tubes by pipetting an amount of plasmid DNA followed by 0.5 ml of protoplast suspension and 0.5 ml 50% PEG (polyethylene glycol, molecular weight 8000: Sigma Chemical Co.) dissolved in F-medium (Krens et al. 1982 *Nature* 296:72–74). Incubations were for 20 min at room temperature. After incubation, 0.33 ml of the protoplast suspension was transferred to each well of a 12-well microculture plate containing a 2 ml block of solidified 0.2% low melting point agarose (Bethesda Research Laboratories) in PCM; this procedure eliminated the need for manual dilution of PEG. Transformed protoplasts were incubated for 20–24 h at 26° C. in the dark. DNA used for transformation was digested with appropriate restriction enzymes according to the recommendations of the manufacturers. The completion of the digestion and the concentration of DNA fragments were estimated by HPLC analysis of the digestion mixture on a PE-TSK DEAENPR column (Kato et al., 1989, *Chromatography Journal*, 478:204–268).

GUS activity determination

After incubation, protoplasts and all liquid from the cell culture were collected into 1.5 ml microcentrifuge tubes. After a brief centrifugation (5 s), the protoplast pellet was suspended in 0.3 ml GUS extraction buffer (Jefferson, 1987, *Plant Mol Bio Rep* 5:387–405) (containing 0.1% Triton X-100), mixed, and centrifuged. Protoplast extracts (0.1 ml) were incubated with 0.6 ml of 1 mM MUG (4 methyl umbelliferyl B-D-glucuronide) in GUS extraction buffer (without 0.1% Triton X-100) at 37° C. Three samples (0.2 ml incubation mixture in 1 ml of 0.2M $Ca_2CO_3$) were used for fluorescence measurements (excitation at 365 nm, emission at 455 nm) in a Perkin Elmer spectrofluorimeter calibrated with standard solutions of methylumbelliferone. GUS activity was estimated from the slope of the line generated from time points and normalized to the protein content determined by the method of Lowry et al. (1951).

DNA analysis

Total DNA was isolated from $5\times10^6$ protoplasts 20 h after transformation. Protoplasts were incubated in PCM medium supplemented with 30 units of DNase for 1 h at 37° C. to digest plasmid DNA that remained in solution. After incubation, protoplasts were centrifuged and the pellet was washed with PCM. DNA was isolated by repeated phenol-chloroform extraction of the protoplast pellet, and precipitated from the aqueous phase with 2 volumes of ethanol. After washing with 70% ethanol and vacuum drying, the DNA pellet was suspended in 10 ul of water. Five microliters of the DNA preparation were mixed with 50 nmol P1 primer (5'-GGGGTTTCTACAGGACG-3'(SEQ ID NO: 1); specific for the GUS coding sequence) and 50 nmol P2 primer (5'-CCTCACAGGCTCATCTCG-3'(SEQ ID NO: 2); specific for the Adh1 promoter sequence), a dNTP mixture (final concentration 0.2 mM each), 5 ul of the 10× polymerase chain reaction (PCR) buffer (Perkin-Elmer Cetus, Emeryville, Calif.), and Tap polymerase (2.5 units per tube).

The $MgCl_2$ concentration of the buffer was adjusted to 2 mM, and the final volume of the reaction was adjusted to 50 ul with water. PCR was carried out in a Perkin-Elmer Cetus DNA thermal cycler. After initial heating at 94° C. for 5 min, 25 cycles of PCR were carried out with denaturation, annealing, and extension steps of 94° C. for 1 min, 45° C. for 1 min, and 72° C. for 2 min, respectively. The extension steps were increased with each cycle by an additional 15 s. Twenty-five microliters of the amplification reaction were loaded on an agarose gel to analyze the products.

For Southern blot analysis, DNA was isolated from transformed protoplasts as described above for PCR. The standard protocols of Maniatis et al., (1982) were used for the DNA electrophoresis, blotting, and hybridization. The radioactive probe was prepared using the Multiprime DNA labeling system of Amersham International according to the manufacturer's instructions. The blot was hybridized with a $^{32}$P-labeled BamHI-SstI fragment of the pPUR plasmid (Lyznik, et al., 1989-gusA coding sequence).

Results

Experimental system

The experimental strategy relied on the supposition that two separate DNA molecules with overlapping homologous regions, would recombine upon introduction into maize protoplasts. The recombination event would result in the positioning of the gusA coding sequences behind the maize Adh1 promoter. The resultant GUS activity would indicate that homologous recombination had occurred between the two plasmids, since neither of the two separate plasmids could express gusA. Both plasmids, pBx26 and piGUS, contained 459 bp of Adh1 intron A to serve as the effective region of homology. Recombination within this region of the plasmid would be expected to yield a functional gusA gene.

GUS expression in transformed protoplasts

The pAeiGUS plasmid was a much more effective construction for GUS expression in maize protoplasts than constructions based only on the Adh1 promoter or the 35 S CaMV promoter. Plasmid pAeiGUS (6.6 kb) was about 1 kb larger than p35SGUS (5.6 kb) and 0.4 kb larger than p35SiGUS (6.2 kb); thus, it is probable that the higher GUS expression from pAei-GUS was due to an increase expression rate rather than increased uptake of DNA into the protoplasts. GUS activity could be observed in maize protoplasts 4 h after transformation with pAeiGUS. The 20–24 h period between transformation and enzyme assay used in experiments reported here was a compromise. This was owing to the need to have a strong signal of GUS activity, but also the need to keep the protoplast incubation time short. Recombination reactions in mammalian systems take place shortly after transformation, and the DNA persists in the nucleus with a half-life of about 20 h. While variability from experiment to experiment was quite high, variability within a single experiment was low.

Evidence of homologous recombination

When maize protoplasts were co-transformed with the products of the EcoRI-PvuII double digestion of pBx26 and HindIII-linearized piGUS DNA, GUS activity was observed after the 20–24 h period of incubation. The transient nature of GUS expression following the recombination between free plasmid molecules was evident in the decline in GUS activity over time. GUS activity was at the background level after protoplast transformation with plasmid DNAs supplied separately. These results indicated that interaction of the two plasmid DNA molecules in the co-transformed protoplasts was required for the detection of GUS activity.

Support for the presence of recombinant DNA molecules in protoplasts was provided by PCR analysis of total DNA isolated from co-transformed protoplasts. The 720 bp DNA amplification product (see the Materials and Methods for details of the two primers used) expected as a result of the recombination reaction was observed when the reaction was carried out in the presence of total DNA isolated from co-transformed protoplasts. The same sized fragment was amplified from total DNA isolated from protoplasts transformed with the control plasmid pAeiGUS, but not from DNA isolated from protoplasts following the treatments with piGUS, pBx26, or mock transformation (no DNA).

The amplification procedure of the polymerase chain reaction can produce recombinant molecules in vitro from piGUS and pBx26 DNA fragments sharing homologous sequences; thus, the observed 720 bp DNA fragment might only partially result from the amplification of recombination products generated inside the co-transformed protoplasts. However, direct analysis of total protoplast DNA on agarose gels followed by blotting and hybridization to a probe of the GUS coding sequence showed that DNA fragments of higher molecular weight than the original transforming DNA and containing the GUS coding sequences were present only in DNA preparations from co-transformed protoplasts. In addition, the linearized piGUS DNA molecules seemed to be more susceptible to degradation than circular pAeiGUS.

A simple ligation of free ends of DNA between restricted pBx26 and piGUS might lead to the activation of the gusA coding sequence. The DNA molecules did recombine (ligate) to activate the gusA gene, but at a very low level. The activity (close to the background level) represented only a small fraction of the GUS activity obtained after co-transformation with plasmid fragments sharing the overlapping effective homologous sequences. The ligation product of the co-transformed EcoRI-PvuII fragment of pBx26 and piGUS linearized with HindIII should yield a fragment longer (1.2 kb) then the 720 bp amplification product obtained in the PCR. Indeed, the main amplification products following co-transformation of pBx26 and piGUS into maize protoplasts was of the size corresponding to the amplified fragment of intact pAeiGUS DNA with other only very minor bands seen in the original gel. GUS activity above the background level was observed after co-transformation with the circular forms of plasmid DNA or with plasmids linearized outside the effective homologous regions but was increased after restriction proximal to or inside the effective homologous regions. These results indicated that the recombination between plasmid molecules was not a random process but, rather, depended strongly on both the lengths of the homologous regions and the positions of the cuts within the DNA sequences.

Other requirements of recombination reactions

Both plasmid DNA molecules had to be linearized to obtain efficient expression of GUS protein; if only one of the plasmids was linearized the level of GUS activity, and hence recombination, was low. In addition, at least one end of the linearized molecule had to share homology with the effective homologous region of the other molecule. The presence of a terminal nonhomologous region of the 3' end of the pBx26 EcoRI-PvuI or EcoRI-AccI fragments strongly reduced GUS activity. In all experiments performed involving pBx26 and piGUS, the highest GUS activity was observed in protoplasts co-transformed with the EcoRI-PvuII fragment of pBx26. This fragment contained the maximum length (459 pb) of the effective homologous region.

Similar digestions of the other recombination substrate, piGUS, did not provide conclusive results. There was no difference in the total length of the effective homologous region between products of different restriction enzyme digestions since all restriction enzymes used piGUS cut only in one place. While HindIII digestion of piGUS produced the highest GUS activity when co-transformed with the pBx26 EcoRI-PvuII fragment, in other experiments StuI-digested piGUS molecules were more efficient. StuI digestion resulted in 113 bp of the effective homologous region at the 5' end of the piGUS DNA as compared to the 459 bp after HindIII digestion. Since the enzyme only cut the plasmid at one site, the products of the StuI restriction contained homologous regions at both ends of the DNA molecule; HindIII digestion resulted in the effective homologous region being only at one end.

Double digestion of piGUS DNA with StuI-BglII and StuI-HindIII or StuI-PvuII; (removal of increasing lengths of the 3'-end terminal homology) resulted in decreased activity of GUS in co-transformed protoplasts as compared to the single digestion with StuI. This effect was observed when the digestion products were separated before co-transformation or when a mixture of restriction fragments was used in co-transformation experiments. Thus, it was unlikely that the observed decrease in GUS activity was due to the interference of the additional digestion products (StuI-BglII or StuI-HindIII short fragments) with the recombination reaction. Once the 3' end of piGUS did not contain a homologous region (HindIII digestion), additional removal of plasmid sequences at this end did not affect the recombination activities.

Discussion

It is shown that homologous recombination occurs between two plasmids following their uptake into maize protoplasts. Use of the gusA reporter gene, the transient expression assay for GUS, and the direct uptake of DNA mediated by PEG made the experimental system rapid, convenient, and reliable. The use of two plasmids, each incapable of expressing gusA alone, but sharing homologous sequences provided by intron A of the adh1 gene of maize, permitted the direct demonstration of homologous recombination through the expression of gusA. By restricting the homologous regions of the two plasmids at different sites, information was obtained concerning recombination reactions. This study has shown that homologous recombination between introduced plasmid DNA can take place in plant protoplasts.

EXAMPLE 2

FLP Mediated Site Specific Recombination between Plasmid FRT sites in Maize and Rice cells Materials and Methods Synthesis of FLP expression vectors The genomic clone of maize adh 1 and the vector of pAeiGUS were described in Example 1. Plasmid pAHC27 was provided by Dr. Peter Quail, University of California, Berkeley. Plasmids pNEOβGAL and pOG44 were purchased from Stratagene, LaJolla, Calif. pUbiGUS was constructed by ligating the maize ubiquitin gene 5' controlling elements in front of the gusA coding sequence by ligation of the XbaI fragment of pAHC27 into HindIII-BamHI restriction sites of p35SGUS. For the construction of pAeiFLP, both pAeiGUS and pOG44 were digested with BglII and SacI. The 1.5 kb fragment carrying the FLP coding sequence from pOG44 was then ligated directly into the eluted 4.4 kb fragment of pAeiGUS replacing the gusA coding sequence. pUbiFLP was obtained by isolating the 1.5 kb SacI-FindIII FLP fragment from pOG44 and subcloning into the respective sites of pGEM-7Z(–)f (Promega, Madison, Wis.)). The resulting plasmid was cleaved with SacI and SmaI, and the 1.5 kb FLP fragment was then ligated directly into SacI-SmaI digested pUbiGUS replacing the gusA fragment with the FLP gene.

Synthesis of FRT containing vectors

Two primers (5'-GTGATCAGAAGTT-CCTATTCCGAAGTTCCTATTCTCTAGAAA-3' (SEQ ID NO: 3)) and (5'-CTGATCAGAAGTTCCTATACTTTCTAGA-3' (SEQ ID NO: 4)) were annealed (4 nmoles each) and incubated with 5 units of T4 DNA polymerase and 60 nmoles of each dNTP in 0.1 ml at 11° C. for 3 hrs. to form a complete FRT recombination site of 48 bp. The primer-extended fragments contained a BclI restriction site on each end. Phosphate groups were then added to the terminal nucleotides by incubation with 20 units of T4 DNA kinase and 16 nmoles ATP in 30 µl of 1× kinase buffer. The resulting double-stranded DNA fragments were blunt-end ligated and cleaved with BclI restriction enzyme. The products were then ligated directly into the BglII site of pUbiGUS forming PUFRTG. For the construction of the pUFRTmG vector, containing a minimal version of the FRT site (37 bp), the primer extended products were blunt-end ligated into the BglII site of pUbi-GUS (the BglII site of pUbiGUS was filled-in using T4 DNA polymerase). Confirmation of the minimal FRT sequence was done by sequencing the double-stranded plasmid DNA. pU2FRTG and pU2FRTmG were constructed by ligation of the 1.3 kb XbaI fragment of pNEOBGAL into pUFRTG and pUFRTmG, respectively. The test plasmid pUbiFRT for intermolecular recombination was constructed by EcoR1 restriction of pU2FRTmG and religation of the resulting plasmid DNA fragments. The other substrate for intermolecular recombination, PFRTGUS, was obtained by digestion of pU2FRTmG with EcoRI and BamHI, isolation of the fragment containing the gusA coding sequence and the FRT site, and ligation of the resulting fragment into the respective sites of pGEM-7Z(−)f (Promega, Madison, Wis.).

Molecular analysis of DNA

Polymerase chain reactions (PCRS) were carried out in a Perkin-Elmer Cetus DNA thermal cycler. Amplification was performed using reagents and protocols as outlined by the Perkin-Elmer Cetus GeneAmp PCR Kit (Perkin-elmer Cetus, Norwalk, Conn.). Sequences of primers were as follows: 5'-CCCCAACCTCGTG-3' (SEQ ID NO: 5) for the first exon of the ubiquitin gene and 5'-GGGGTTTCTACAGGACG-3' (SEQ ID NO:1) for the 5' end of the gusA coding sequence. PCR reactions contained: 5 µl of template DNA, 5 µl of primer solution (50 nmoles each), 5 µl of 10× PCR buffer II (22), 2.0 µl dNTPs mix (final concentration 200 µM of each nucleotide), and 0.25 µl of Tag polymerase (2.5 units/100 µl) in a final volume of 50 µl. Denaturation, annealing, and extension steps were performed at 94° C. for 1 minute, 45° C. for 1 minute, and 72° C. for 2 minutes, respectively. The extension steps were increased 15 seconds with each cycle. Five microliters of each amplified product were analyzed using 1.0% agarose gel electrophoresis.

Southern blotting of agarose gels containing PCR amplified DNA was performed using capillary transfer to Hybond-N membrane (Amersham, Arlington Heights, Ill.). DNA was fixed to the membrane by UV irradiation and incubated in prehybridization solution (5× SSPE, 5× Denhardt's solution, 0.5% SDS) at 65° C. for 4 hours. The radioactive probe ($\alpha$ $^{32}$P-labeled SmaI- BglII fragment isolated from pUbiGUS) was prepared using the Multiprime DNA labeling system according to the manufacturer's instructions (Amersham, Arlington Heights, Ill.). The probe contained the complete ubiquitin intron and part of the fist exon. The blot was hybridized overnight in prehybridization solution at 65° C. and subsequently processed according to standard procedures.

The nucleotide sequences of the FRT sites were determined by a modified dideoxy method using Sequenase Version 2.0 (United States Biochemical Cleveland, Ohio). CsCl purified pUFRTG and pU2FRTmG plasmid DNA was used as template DNA. The primer used was the same as that used for PCR which annealed to the 5' end of the fist exon of the ubiquitin gene.

Transformation procedures

The cell suspension culture of maize (Zea mays L.) was initiated from A188 x BMS type II callus and maintained (Kamo et al. 1987, Planta, 172, 245–251). Seven days prior to protoplast isolation, 2 ml packed cell volume (PCV) of the suspension culture was transferred into 37 ml of MS medium (Murashige et al., 1962, Physical Plant, 15, 473–497) supplemented with 3.5 mg/l 2,4-D.

Approximately 5 ml PCV of suspension cells were digested for 3 h in 20 ml MS medium containing 0.2M mannitol, 0.5 mg/l thiamine, 2 mg/l 2,4-D, 80 mM $CaCl_2.2H_2O$, 2% cellulase, 0.25% pectinase, and 0.1% pectolyase Y-23, pH 6.0 Protoplasts were filtered through a 48 µm nylon mesh screen and pelleted by centrifugation at 50×g for 15 minutes. The pellet was suspended in 8 ml of protoplast culture medium (PCM containing 9% Ficoll 400 and overlaid with 4 ml of transformation medium (TM). The transformation medium consisted of 100 mM MES buffer, pH 5.5, 0.2M mannitol, and 80 mM $CaCl_2.H_2$. Following centrifugation at 75×g for 10 minutes, a band of protoplasts was collected from the interphase, and the concentration was adjusted to $1.0 \times 10^7$ protoplasts/ml with TM.

Protoplast transformation was performed in 12 ml Falcon polystyrene tubes by pipetting 20–25 µl of plasmid DNA (1.0 mg/ml) followed by 0.5 ml of protoplasts and 0.5 ml of 50% PEG (polyethylene glycol, MW=8000; dissolved in F-solution. Protoplasts were incubated for 20 minutes at room temperature. After incubation, 330 µl of the protoplast solution were transferred to a 12-well microculture dish containing 2 ml solidified 0.8% low melting point agarose in PCM. Plates were then wrapped with Parafilm and incubated at 25° C. in the dark for approximately 24 hours.

GUS Activity and Protein Determination

Following the 24 hrs. incubation, protoplasts were collected and resuspended in 300 µl of GUS extraction buffer containing 0.1% Triton X-100. After centrifugation at 16,000×g for 5 minutes, a 25 µl extract of the protoplasts was incubated with 150 µl of 1 mM MUG (4-methyl umbelliferyl β-D-glucuronide) in GUS extraction buffer in a 96-well plate at 37° C. Reactions were stopped at various times by adding 125 µl of GUS stop buffer (0.2 $MCaCO_3$). Fluorescence (excitation at 362 λ and emission at 455 λ) was measured in a Perkin Elmer Luminescence Spectrometer LS50B calibrated with standards of methyumbelliferone. GUS activity was calculated from the slope of the line generated from time points and normalized to the protein content determined by the method of Bradford, 1976, Anal. Biochem., 72, 248–254.

Results

The FLP/FRT site-specific recombination system used in these studies consists of two elements: plasmid DNA encoding for the FLP enzyme and test plasmids containing the FRT recombination sites (FIGS. 3A–B and 4A–B).

The target FRT nucleotide sequence consists of three recreated DNA sequences of 13 bp each; two repeats in a direct orientation and one repeat inverted relative to the other two. In addition, there is an 8 bp spacer region between the repeats which determines the orientation of the FRT recombination site and which serves as the site of sequence pairing that initiates the recombination event. The FLP recombinase binds to all three repeats, anneals DNA sequences within spacer regions of two FRT sites, cleaves the sites at the borders of the spacer, and exchanges the DNA strands. Depending on the orientation of the recombination sites, the DNA fragment between the FRTs can be either inverted or excised. Additionally, the FLP recombinase can act on target FRT sites located on separate DNA molecules. These intermolecular recombinations can lead to integration of foreign DNA into FRT sites in bacterial and mouse genomes.

FIG. 3 illustrates the strategy and diagram of the FLP expression vectors used to study activity of yeast FLP/FRT system in plant protoplasts. More particularly FIG. 3A shows components of the recombination system to test the DNA excision reaction catalyzed by the FLP protein. FLP enzyme can be produced by either pAeiFLP or pUbiFLP. FIG. 3B shows the sequence of the splicing site of the original Adh1 genomic clone (SEQ ID NO: 6) and the sequence of the junction sites between cloned FLP coding sequence and Adh1 (SEQ ID NO: 7) or ubiquitin maize (SEQ ID NO: 8) promoters. Thick lines indicate an open reading frame of Adh1 gene or the translation start codon for FLP protein synthesis in the pUbiFLP vector. Note that the first exon of the maize ubiquitin gene in contrast to the Adh1 first exon is not translated.

FIG. 4 illustrates the structure of the FRT site-containing vectors. A single complete (SEQ ID NO: 9) or partial (SEQ ID NO: 10) FRT site was ligated into the BglII site of the ubiquitin first exon. Asterisks show the FLP binding sites. Arrows denote 13 bp inverted repeats. pUFRTmG vector contained only one 13 bp repeat and one shorter 11 bp inverted repeat. This FRT site lacks additional five FLP protein binding sites. Insertion of the XbaI fragment of pNEOβGAL into the XbaI site of the FRT vectors provided the second FRT site and led to inactivation of GUS expression.

Figure 3A:
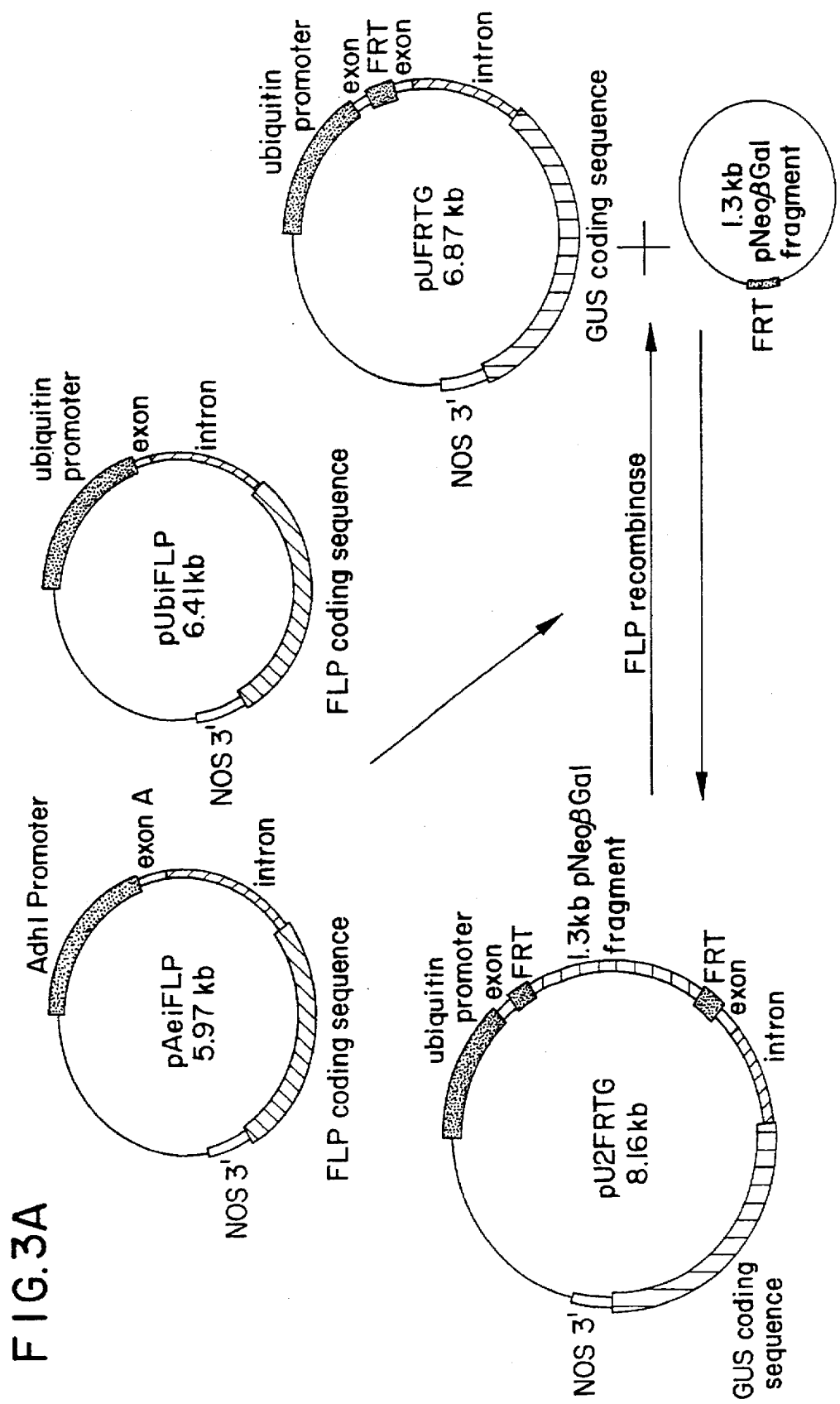
FIGS. 3A and 3B are diagrammatic representations of FLP expression vectors used to study activity of yeast FLP/FRT system in plant protoplasts.
Figure 3B:
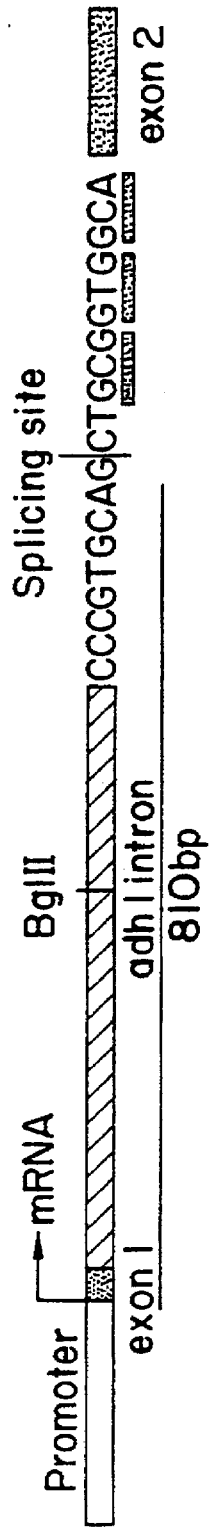
Figure 3B:
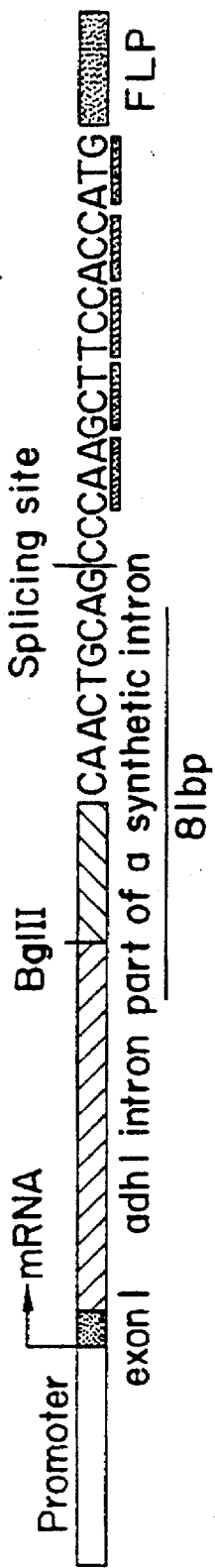
Figure 3B:
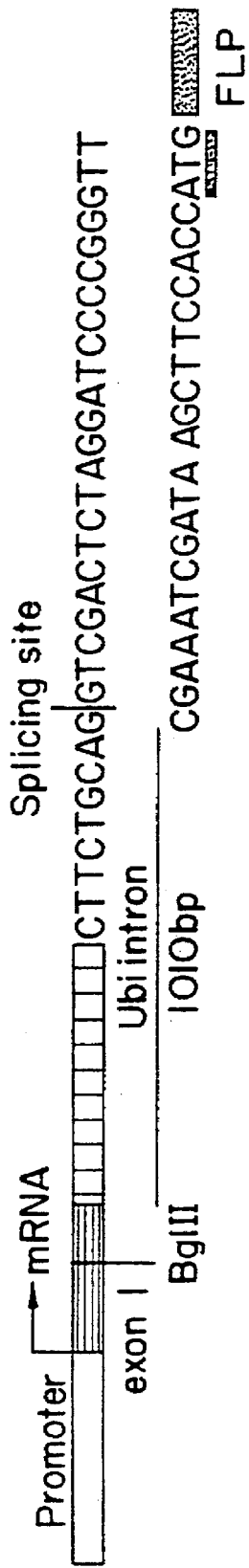

The FLP recombinase expressed from FLP vectors should recombine test plasmid DNA within the FRT target sites to restore expression of GUS enzyme. Expression of the FLP gene was driven by the maize adh1 promoter in pAeiFLP and by the maize ubiquitin promoter in pUbiFLP (FIG. 3B). Both constructs included the first exon and intron of the respective genes. In the pAeiFLP construction, the first intron contained 290 bp of the first adh1 intron fused at the BglII site to 81 bp of the synthetic intron from pOG44. Both promoters proved to be very effective as determined in transient GUS expression assays of maize protoplasts; however, the ubiquitin promoter was superior.

The BglII site of the first exon of the ubiquitin promoter in pUbiGUS was chosen for insertion of the FRT sequences following initial screening of other appropriate insertion sites. Two different FRT sites were ligated into the BglII site—one minimal 37 bp FRT site referred to as FRTm and one complete 48 bp FRT site referred to as FRT (FIG. 4A). The FRTm site lacks the third repeat which includes five additional FLP protein binding sites; however, a similar FRT deletion (missing one repeat and the same FLP protein binding sites) has been shown to be as effective as the wild-type FRT site in vitro. Interestingly, insertion of the FRTm site into the pUbiGUS resulted in higher expression of the GUS enzyme. Insertion of the full length FRT site resulted in reduction of GUS expression.

A second FRT site for intramolecular recombination of test plasmids was created by insertion of the XbaI fragment of pNEOβGAL into the single XbaI site of pUFRTG. Insertion of the pNEOβGAL fragment provided supplemental sequences to form an additional FRT site and a 1.31 kb spacer DNA which separated the ubiquitin promoter from the gusA coding sequence (FIG. 4B). As a result, GUS activity in maize protoplasts transformed with pU2FRTG was substantially reduced. The reverse orientation of the ligated XbaI fragment of pNEOβGAL should also inactivate GUS expression but should not form functional FRT sites. pU2FRTmG rev. and pU2FRTG rev. vectors were used to demonstrate that fully functional FRT sites were required to obtain activation of GUS expression by the FLP protein.

Transient GUS activity in maize protoplasts co-transformed with pAeiFLP and pU2FRTmG was higher than in protoplasts transformed with only pU2FRTmG. The restored GUS expression was approximately 10% of that observed after protoplast transformation with the control pUFRTmG. GUS activity in was maize protoplasts transformed with pAeiFLP was similar to background GUS activity. Thus, the FLP/FRT recombination system appeared to function in maize protoplasts. This was further substantiated by the increase of GUS activity in maize protoplasts co-transformed with increasing amounts of pAeiFLP DNA. This indicated not only that GUS expression is dependent on the amount of the FLP enzyme present, but also that the amount of the FLP protein might have been the limiting factor in the recombination process. When pUbiFLP was introduced into maize protoplasts along with the test plasmids, GUS activities were restored for both pU2FRTmG and pU2FRTG to 81% and 45% of the respective control treatments. Reactivation of GUS in the presence of pUbiFLP and the vectors containing both FRT's indicated that FLP protein catalyzed excision of the 1.31 kb fragment. When the FRT's were mutated by the reverse ligation of the 1.31 kb fragment (pU2FRTmG rev. and pU2FRTG rev.), GUS activity was not restored indicating that these FRT sites were not recognized by the FLP protein.

To observe intermolecular recombination at the FRT sites, the ubiquitin promoter or the gusA coding sequence was removed from pUFRTmG to form pUbiFRT and pFRTGUS, respectively. Introduction of two different FRT sites into protoplasts on two separate DNA molecules (pUbiFRT and PFRTGUS) produced approximately a 4-fold increase in GUS activity above background activity in protoplasts transformed with pFRTGUS alone. This activity was 15% of the positive control (protoplasts transformed with pUFRTmG). The relatively high background expression of GUS in pFRT-GUS transformed protoplasts (6±1 unit) might be the result of the entire first intron and part of the ubiquitin first exon being present in this vector.

The FLP/FRT recombination system has also been tested in rice protoplasts. The recombinase-mediated excision of DNA proved to be as effective in rice as in maize protoplasts. The same pattern of response was observed for the different plasmid constructions containing FRTs. Co-transformation of rice protoplasts with pUbiFLP and either pU2FRTmG or pU2FRTG gave 75% and 31% restoration of the control GUS activity. Vectors containing inactive FRT sites gave only 1–2% of the control GUS activity.

PCR analysis of total DNA isolated from co-transformed maize protoplasts indicated the presence of recombinant plasmid DNA molecules. The two primers used for this analysis amplify the region between the ubiquitin transcription start and the 5' end of the gusA coding sequence. The length of this region is 2.49 kb in pU2FRTGm and pU2FRTG. After removal of the 1.31 kb fragment as a result of the recombination reaction, the amplified region should be reduced to 1.18 kb and should then be equivalent to the amplification product of pUFRTG DNA. A 1.18 kb fragment was identified in the products of the PCR reaction using total DNA isolated from maize protoplasts co-transformed with pU2FRTmG and pUbiFLP as a template. The identity of this fragment was confirmed through hybridization using a probe specific to the first intron of the ubiquitin gene.

Discussion

The results presented here show that the FLP recombinase of yeast can promote the site-specific recombination between FRT sites in both maize and rice cells. This conclusion is based on the following evidence. Transient expression of the GUS enzyme from recombination test vectors increased in protoplasts co-transformed with functional FLP expression vectors, and the magnitude of this increase depended on the amount of co-transformed plasmid DNA containing the FLP gene. Additionally, higher expression of GUS protein in co-transformed protoplasts was observed when a stronger promoter was used to drive expression of the FLP protein. The increase in GUS expression was abolished if the FRT sites in test vectors were mutated. Lastly, the products of the site-specific recombination reaction were identified in co-transformed protoplasts.

EXAMPLE 3

Integrative Recombination

Figure 5:
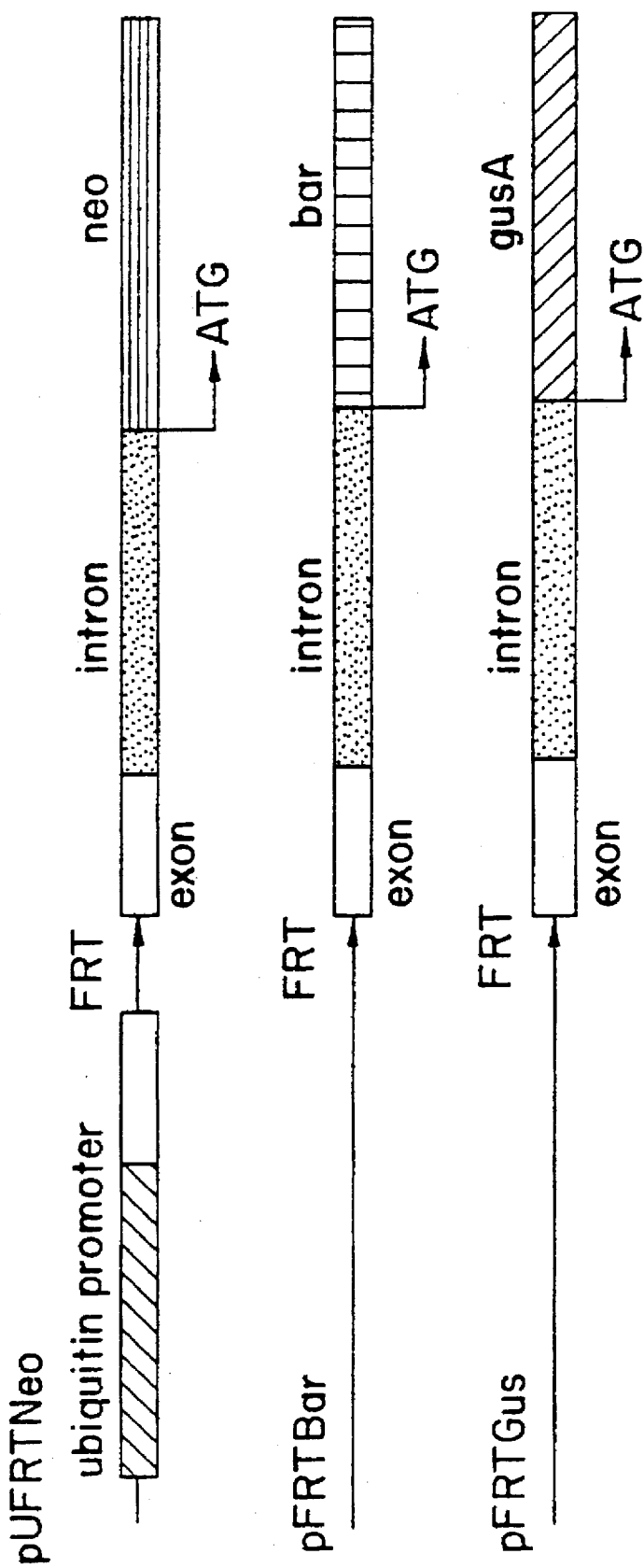
FIG. 5 depicts vectors useful for testing integrative recombination.

To test the efficiency of insertion recombination reactions, DNA constructs containing an FRT site integrated into a selectable marker gene are designed and synthesized. Upon introduction of these constructs into maize protoplasts followed by the selection of transformed calli, only material containing the integrated FRT sites is selected. The neomycin phosphotransferase neo gene is used as a selectable marker and the 5' controlling elements (promoter) of the maize polyubiquitin gene is used to make pUFRTNeo (FIG. 5).

The neo gene has proven to be a reliable selectable marker for maize protoplasts, and the ubiquitin promoter assures a high level of foreign gene expression in transformed maize protoplasts. The coding sequence of the neo gene is not modified, but instead, the FRT site is ligated into the first untranslated exon of the ubiquitin leader sequence. This modification of the first exon does not abolish activity of the ubiquitin promoter.

Neomycin phosphotransferase activity and the copy number of integrated neo genes are determined in selected calli. Individual callus are selected (each containing a different number of active neo gene(s)) and used to establish suspension cultures.

Protoplasts isolated from these suspension cultures are re-transformed with DNA constructs containing a second FRT site and an inactive selectable marker. A plasmid DNA construction containing a promoterless bar gene that retains the first exon and intron of the maize ubiquitin leader sequence and an integrated FRT sequence (pFRTbar) is utilized. Re-transformed protoplasts are selected on medium containing phosphinothricin (PPT); only cells expressing the bar gene inactivate PPT and survive. The FLP recombinase activity is provided by co-transformation of protoplasts with the pUbiFLP plasmid DNA (described in Example 2). As a negative control, protoplasts are re-transformed with a construct similar to the pFRTbar construct except lacking the FRT site. Results are adjusted for activation of the bar gene due to spurious random integrations or homologous recombination within the ubiquitin first intron sequences.

Phosphinothricin-resistant calli are obtained as a result of FLP catalyzed site-specific recombination between FRT sites which places the ubiquitin promoter in close proximity to the bar gene. The efficiency of this reaction is analyzed by at least two methods. For calli containing a single or a few genomic DNA integrated FRT sites, the number of PPT-resistant calli produced after re-transformation with pFRTbar versus the number of PPT-resistant calli obtained after retransformation with the pFRTbar construct lacking a FRT site, should indicate the efficiency of the site specific recombination process. Results are also compared to the transformation efficiency of protoplasts transformed with a DNA construct containing the active bar gene (pUFRTbar), and to the co-transformation efficiency in the presence and absence of the pUbiFLP construct (to test the requirement of the FLP recombinase activity).

For protoplasts containing many copies of the FRT sites, an alternative method for assessing the recognition efficiency of the FLP recombinase for genome-integrated FRT sites involves the analysis of bar gene integration patterns. This method requires the selection of re-transformed protoplasts on PPT medium, which results in both bar+ neo– phenotypes (if all neo genes are inactivated) and bar+neo+ phenotypes (if only some of the neo genes are inactivated). All PPT-resistant calli can be conveniently screened for neo activity using a recently modified microplate assay (Peng. et al., 1993, Plant Mol Biol Rep, in press). It is not necessary to make adjustments for re-transformation or co-transformation efficiencies since the product of a single transformation event is being analyzed. The fraction of integrated FRT sites recognized as a site of bar gene integration indicates the effectiveness of the recombination reaction per se as well as the effectiveness of the communication network between DNA sequences inside the plant nucleus. Several primary FRT transformed callus cell lines are tested to assess the influence of genomic position of the FRT sites on the recognition efficiency of integrated FRT sites by the FLP recombinase. Site-specific integrations of the bar genes are verified and analyzed by Southern blotting and PCR.

EXAMPLE 4

Excisional Recombination

One goal of the excisional recombination experiments is to determine the maximum distance between the two FRT sites that will still allow efficient excision by the recombinase. This maximum distance is determined through the use of the pU2FRTGUS DNA construct. This DNA construct contains a 1.3 kb DNA fragment with a unique BamHI restriction site located between the two FRT sites. The BamHI restriction site allows for the insertion of additional DNA sequences to increase the distance between the two FRT sites. The efficiency of the excision reaction, relative to the distance between the two FRT sites, is evaluated using the transient GUS expression assay.

Two different methods can be used to evaluate the efficiency of the FLP recombinase in the excision of integrated foreign genes: retransformation and controlled expression of the recombinase gene.

Re-transformation

Figure 6:
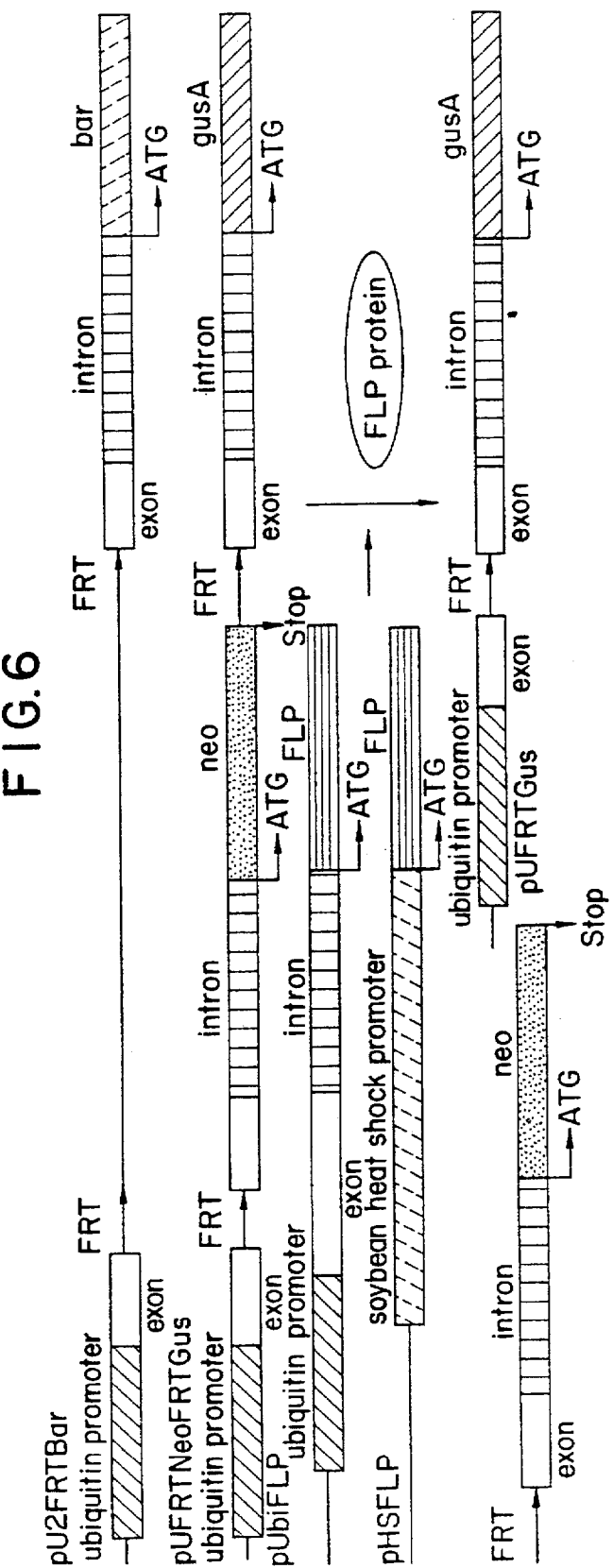
FIG. 6 provides diagrams of vectors for testing excisional recombination.

In the first method, maize protoplasts are transformed with a DNA construct containing the gusA gene inactivated by insertion of the neo gene into the promoter region of the gusA gene (pUFRTNeoFRTGus). The neo gene is positioned between two directly-repeated FRT sites and is expressed (FIG. 6).

Selection of transformed protoplasts on medium with kanamycin results in transgenic calli with a neo+ gus– phenotype. These calli serve as initial material to establish new suspension cultures. Protoplasts isolated from these suspension cultures and re-transformed with the pUbiFLP DNA construct excise the neo gene and thus yield gus+ phenotypes, which can be detected in transient assays. These relatively simple experiments provide information about the existence of the excision reaction catalyzed by the FLP protein in plant cells.

Controlled Expression of the FLP Gene

Figure 8:
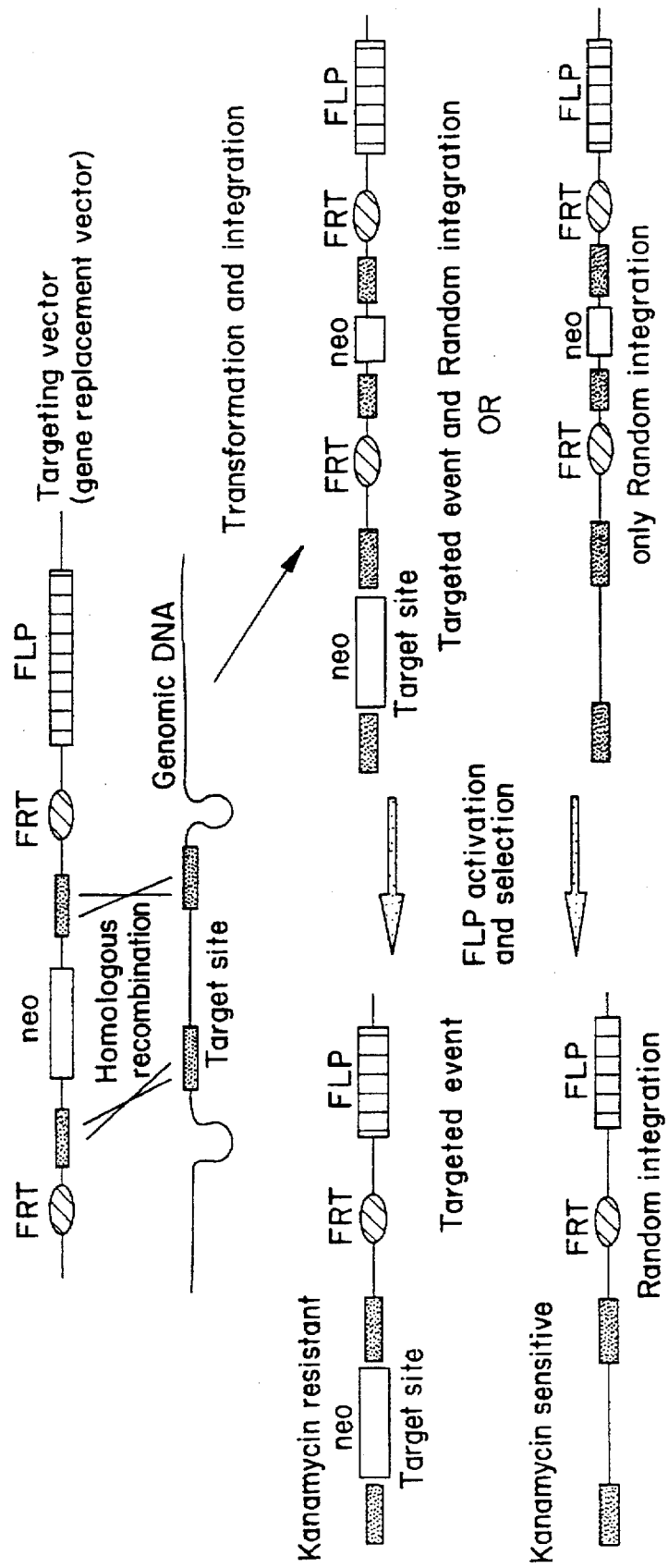
FIG. 8 provides a schematic map for a targeting vector in accordance with the present invention.

In the second approach, expression of the FLP gene is controlled to achieve excision so as to eliminate the re-transformation step in favor of controlling the FLP recombinase activity. Maize protoplasts are co-transformed with the pUFRTNeoFRTGus plasmid DNA and plasmid constructions containing the FLP gene under control of the soybean heat shock inducible promoter. Studies of the activity of the soybean Gmhsp 17.5-E gene promoter in maize protoplasts and cells showed excellent performance of this promoter in response to heat shock treatment. The background activity at 24° C. was low and a several fold increase of activity was observed after heat shock at 42° C. for 0.5–1 hour. The DNA construct containing the FLP gene under the control of this heat shock promoter was made (PHSFLP) and tested in transient assays for site-specific recombination (Table 1).

made in which an active neo gene with its own promoter (the CaMV 35S promoter) is inserted into the cloned adh1 homologous region. The second element of the site-specific recombination system—the FLP gene—is positioned outside the plasmid DNA region encompassed by the FRT sites. A schematic drawing of the targeting DNA construct is presented in FIG. 8.

Maize protoplasts isolated from a A188×BMS suspension culture are transformed with the targeting DNA construct using the PEG-mediated transformation technique. The plasmid DNA is linearized outside the adh1 homologous region to produce a sequence replacement rather than a sequence insertion DNA construct. Transformed protoplasts are selected on medium with kanamycin.

DNA of the sequence insertion construct integrates into the genomic DNA via homologous recombination, and kanamycin resistant calli are recovered. These double reciprocal recombination events lead to replacement of the genomic adh1 DNA sequences with the neo gene of the plasmid DNA. Alternatively or simultaneously, the entire plasmid molecule integrates randomly through a random recombination mechanism. Any random integration event leads to expression of the FLP gene thus causing excision of

TABLE 1

| Vector used for transformation | GUS activity nmol MU/min/mg protein Heat shock (hrs) | | | GUS activity corrected for pU2FRTmG background Heat shock (hrs) | | | GUS activity corrected for pUFRTmG expression Heat shock (hrs) | | | GUS activity corrected for pUbiFLP expression Heat shock (hrs) | | |
|---|---|---|---|---|---|---|---|---|---|---|---|---|
| | 0 | 0.5 | 1 | 0 | 0.5 | 1 | 0 | 0.5 | 1 | 0 | 0.5 | 1 |
| -DNA | 0.06 | | | | | | | | | | | |
| pUFRTmG | 58 | 41 | 41 | 58 | 41 | 41 | 58 | 58 | 58 | 58 | 58 | 58 |
| pU2FRTmG | 0.6 | 0.6 | 0.4 | 0 | 0 | 0 | 0 | 0 | 0 | 0 | 0 | 0 |
| + pUbiFLP | 58 | 33 | 20 | 58 | 33 | 20 | 58 | 47 | 28 | 58 | 58 | 58 |
| + pHSFLP | 0.8 | 8.4 | 9.1 | 0.2 | 7.8 | 8.7 | 0.2 | 11.1 | 12.4 | 0.2 | 14.0 | 24.8 |

There still remains the possibility that the residual FLP activity at room temperature might be too high, which could lead to excision reactions prior to the heat shock treatment. Modifications to the transformation procedure are made as necessary, such as growing the transformed protoplasts and cells at lower temperatures.

Once stably transformed calli are selected on medium containing kanamycin, the heat shock treatment activates the FLP gene leading to the excision of the neo gene and activation of the gusA gene. Three different phenotypes are generated: neo+gus−, neo+gus+, neo−gus+. The relative frequency of these phenotypes in relation to the copy number of integrated plasmid molecules provides an estimate of the efficiency of the excision reaction.

EXAMPLE 5
Gene Targeting and Excision of Foreign DNA

Figure 7:
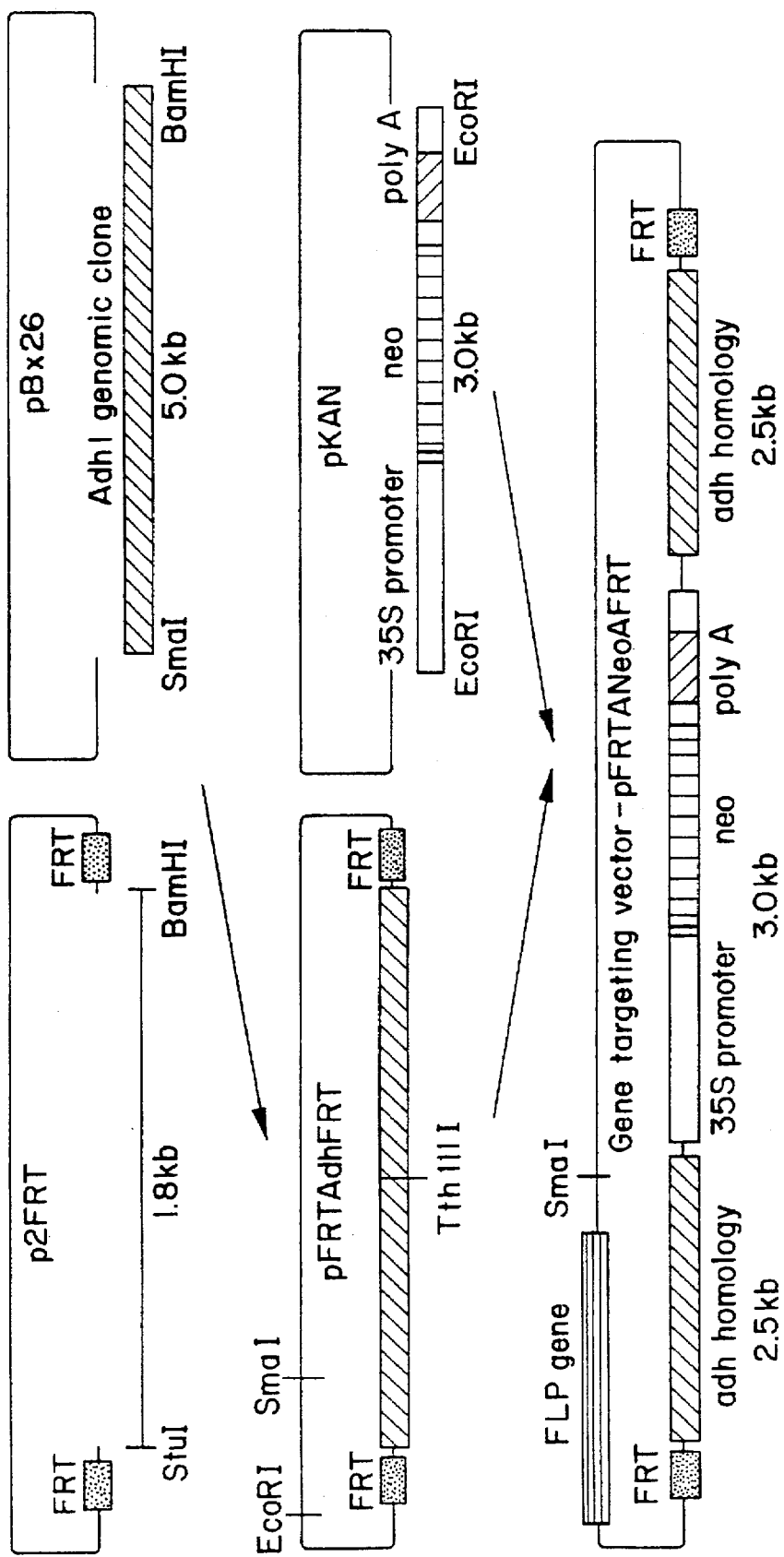
FIG. 7 illustrates the general strategy for a positive selection of gene targeting events using the FLP/FRT site-specific recombination system.

A strategy is developed as illustrated in FIG. 7 to use the FLP/FRT system to positively select from gene targeting events and at the same time eliminate any randomly integrated foreign plasmid DNA.

The adh1 locus of the maize genome is well characterized. The adh1 locus is used as a target site. DNA fragments of the adh1 genomic clone, about 5 kb in length, is ligated between two directly-repeated FRT sites. Gene targeting experiments on animal systems indicate that the efficiency of gene targeting increases exponentially with increasing length of the homologous regions on plasmid DNA molecules, but reaches a saturation at about 4 kb. A plasmid construct is the randomly integrated neo gene. Excision of the neo gene renders those cells sensitive to kanamycin and they subsequently die. Only those cells containing the neo gene residing within the genomic adh1 locus, as a result of homologous recombination, retain the resistance to kanamycin, and survive. The selected kanamycin-resistant calli are recovered and the DNA insertion events are analyzed by Southern blotting and/or the polymerase chain reaction to verify and demonstrate the occurrence of the targeting events.

The FLP gene is positioned outside the DNA sequences flanked by the FRTS. This is due to the concern that the efficiency of excisions may be compromised if the FRT sites are separated by too great a distance. The FRT sites are separated by approximately 5.0 kb of DNA sequence in yeast 2 μm plasmid DNA. This natural configuration of the FRT sites for the FLP activity should be considered as an acceptable first approximation. The transient assays for testing the efficiency of excision yield information about the flexibility of the FRT/FLP recombination system with regard to the distance between the FRT sites in maize cells. Where larger distances are tolerated by the recombinase, then the FLP gene and other components can be included with the DNA sequences flanked by the FRT sites.

FIG. 9 illustrates several examples of vectors in accordance with this invention adapted to control gene targeting and gene excisions using recombinases and inducible promoters.

We claim:

1. A DNA construct for transforming a eukaryotic cell, said construct comprising a multifunctional DNA sequence flanked by a pair of directly repeated site-specific recombination sequences, said multifunctional DNA sequence comprising a gene encoding a selectable marker, and a DNA sequence of interest, wherein said DNA sequence of interest is flanked by nucleotide sequences sharing homology to a predetermined nucleotide sequence present in the eukaryotic cell, and said DNA sequence of interest being targeted for insertion via homologous recombination into the DNA of the eukaryotic cell, and the selectable marker gene is operably linked to a regulatory sequence that expresses the gene in the eukaryotic cell.

2. The DNA construct of claim 1, wherein the selectable marker gene and the DNA sequence of interest are both flanked by nucleotide sequences sharing homology to a nucleotide sequence present in the eukaryotic cell.

3. The DNA construct of claim 2, wherein the multifunctional DNA sequence further comprises
   a gene encoding a site specific recombinase that recognizes the site-specific recombination sequences flanking the multifunctional DNA sequence.

4. A DNA construct for inserting a DNA sequence of interest into the DNA of a eukaryotic cell, said construct comprising
   a multifunctional DNA sequence flanked by a pair of directly repeated first site-specific recombination sequences,
   said multifunctional DNA sequence comprising a gene encoding a first site specific recombinase that recognizes the first site-specific recombination sequence, and a DNA sequence targeted for insertion via homologous recombination into the DNA of the eukaryotic cell,
   said target DNA sequence being flanked by nucleotide sequences sharing homology to nucleotide sequences present in the eukaryotic cell, and comprising said DNA sequence of interest and a excisable selection region,
   said excisable selection region being flanked by a pair of directly repeated second site-specific recombination sequences and comprising a gene encoding a selectable marker, and a gene encoding a second site specific recombinase gene that recognizes the second site-specific recombination sequence,
   wherein each gene is operably linked to a regulatory sequence that expresses the gene in the eukaryotic cell.

5. The DNA construct of claim 4 further comprising a DNA sequence that replicates the DNA molecule in a bacterial host, and a DNA sequence encoding a bacterial selectable marker.

6. The DNA construct of claim 4, wherein expression of at least one of the first or second site specific recombinase gene is regulated by an inducible promoter.

7. The DNA construct of claim 6, wherein the expression of the recombinase gene is regulated by the glucocorticoid system.

8. A DNA construct for transforming eukaryotic cells, said construct comprising a multifunctional DNA sequence flanked by a pair of directly repeated site-specific recombination sequences, said multifunctional DNA sequence comprising a polylinker region wherein said polylinker region is flanked by nucleotide sequences sharing homology to a predetermined nucleotide sequence present in the eukaryotic cell, and said polylinker being targeted for insertion via homologous recombination into the DNA of the eukaryotic cell.

9. The DNA construct of claim 8 wherein said multifunctional DNA sequence further comprises a gene encoding a selectable marker.

10. The DNA construct of claim 9 wherein said multifunctional DNA sequence further comprises a gene encoding a site specific recombinase that recognizes the site-specific recombination sequences flanking the multifunctional DNA sequences.

11. The DNA construct of claim 10, wherein the expression of the site specific recombinase gene is regulated by an inducible promoter.

12. The DNA construct of claim 9 further comprising a DNA sequence that replicates the DNA molecule in a bacterial host, and a DNA sequence encoding a bacterial selectable marker.

13. A DNA construct for transforming eukaryotic cells, said construct comprising
    a multifunctional DNA sequence flanked by a pair of directly repeated first site-specific recombination sequences,
    said multifunctional DNA sequence comprising a DNA sequence targeted for insertion via homologous recombination into the DNA of the eukaryotic cell,
    said targeted DNA sequence being flanked by nucleotide sequences sharing homology to nucleotide sequences present in the eukaryotic cell, and comprising a polylinker region and a excisable selection region,
    said excisable selection region being flanked by a pair of directly repeated second site-specific recombination sequences, wherein the second site specific recombination sequence is different than the first site specific recombination sequence, and comprising a gene encoding a selectable marker,
    wherein each gene is operably linked to regulatory sequences that express the gene in the eukaryotic cell.

14. The DNA construct of claim 13, wherein said multifunctional DNA sequence further comprises a gene encoding a first site specific recombinase that recognizes the first site-specific recombination sequences flanking the multifunctional DNA sequence.

15. The DNA construct of claim 14, wherein said excisable selection region further comprises a gene encoding a second site specific recombinase that recognizes the second site-specific recombination sequences flanking the excisable selection region.

* * * * *

UNITED STATES PATENT AND TRADEMARK OFFICE
CERTIFICATE OF CORRECTION

PATENT NO. : 5,744,336
DATED : April 28, 1998
INVENTOR(S) : Thomas K. Hodges et al.

It is certified that error appears in the above-indentified patent and that said Letters Patent is hereby corrected as shown below:

Column 1. line 1 please insert

--Government Rights
This invention was made with United States Government support under Grant No. 91-37301-6375, awarded by the USDA. The United States Government has certain rights to the invention.--

Signed and Sealed this

Ninth Day of February, 1999

Attest:

*Attesting Officer*

*Acting Commissioner of Patents and Trademarks*